United States Patent
Greene et al.

(10) Patent No.: US 6,265,535 B1
(45) Date of Patent: Jul. 24, 2001

(54) PEPTIDES AND PEPTIDE ANALOGUES DESIGNED FROM BINDING SITES OF TUMOR NECROSIS FACTOR RECEPTOR SUPERFAMILY AND THEIR USES

(75) Inventors: Mark I. Greene, Penn Valley; Ramachandran Murali, Drexel Hill, both of PA (US); Wataru Takasaki, Saitama (JP)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 08/866,545

(22) Filed: May 30, 1997

(51) Int. Cl.$^7$ .................................................. A61K 38/12
(52) U.S. Cl. ........................... 530/317; 530/321; 530/326
(58) Field of Search .................................... 530/326, 317, 530/327

(56) References Cited

FOREIGN PATENT DOCUMENTS 0 045 665    6/1982  (EP).

OTHER PUBLICATIONS

Almquist et al., Synthesis and Biological Activity of a Ketomethylene Analogue of a Tripeptide Inhibitor of Angiotensin converting Enzyme, *J. Med. Chem.*, 1980, vol. 23, pp. 1392–1398.

Baker et al., Control of Established Experimental Allergic Encephalomyelitis by inhibition of tumor necrosis factor (TNF) Activity Within the Central Nerous System Using Monoclonal Anitbodies and TNF Receptor–immunoglobulin fusion Proteins, *Eur. J. Immunol.* 1994, vol. 24, pp. 2040–2048.

Banner et al., Crystal Structure of the Soluble Human 55 kd TNF Receptor–Human TNFβ Complex: Implications for TNF Receptor Activation, *Cell*, May 7, 1993, vol. 73, pp. 431–445.

Baumgartner et al., Double–Blind Placebo–Controlled Trial of Tumor Necrosis Factor Receptor (p80) Fusion Protein (TNFRc) in Active Rheumatoid Arthristis, *Arthritis & Rheumatism*, 1996, vol. 39 (Suppl.), p. S74.

Beutler et al., Unraveling Function in the TNF Ligand and Receptor Families, *Science* 1994, vol. 264, pp. 667–668.

Beutler et al., An Evolutionary and Functional Approach to the TNF Receptor/Ligand Family, *Ann. NY Acad. Sci.*, 1994, vol. 730, pp. 118–133.

Döring et al. Identification and Characterization of a TNFα Antaonist Derived From a Monoclonal Antibody, *Mol. Immunol*, 1994, vol. 31, pp. 1059–1067.

Gruss et al., The TNF Ligand Superfamily and Its Relevance for Human Diseases, *Cytokines and Molecular Therapy*, 1995, Vo. 1, pp. 75–105.

Holladay et al., Synthesis of Hydroxyethlene and Ketomethylene Dipeptide Isosteries, *Tetrahedron Lett.*, 1983, vol. 24, pp. 4401–4404.

Hudson et al., Methionine Enkephalin and Isosteric Analogues, *Int. J. Peptide Protein Res.*, 1979, vol. 14, pp. 177–185.

Hruby et al., Conformational Restrictions of Biologically Active Peptides Via Amino Acid Side Chain Groups, *Life Sciences*, 1982, vol. 31, pp. 189–199.

Hann, On the Double Bond Isostere of the Peptide Bond: Preparation of an Enkephalin Analogue, *J. Chem. Soc. Perkin Trans. I.*, 1982, vol. 1, pp. 307–314.

Jennings–White et al., Synthesis of Ketomethylene Analogs of Dipeptides, *Tetrahedron Lett.*, 1980, vol. 23, pp. 2533–2534.

Lorenz et al., In Vivo Blockade of TNF–α by Intravenious Infusion of a Chimeric Monoclonal TNF–α Antibody in Patients with Rheumatoid Arthritis, *J. Immunol.*, 1996, vol. 156, pp. 1646–1653.

Morley, Modulation of the Action of Regulatory Peptides by Structural Modification, *Trends pharm. Sci.*, 1980, vol. 1, pp. 463–468.

Naismith et al., Modularity in the TNF–receptor Family, *TIBS*, Feb. 1998, pp. 74–79.

Peppel et al., A Tumor Necrosis Factor (TNF) Receptor–IgG Heavy Chain Chimeric Protein as a Bivalent Antagonist of TNF Activity, *J. Exp. Med.* 1991, vol. 174, pp. 1483–1489.

Ponder et al., Tertiary Templates for Proteins, *J. Mol. Biol.* 1987, vol. 193, pp. 775–791.

Spatola, "Peptide Backbone Modifications", *Chemistry and Biochemistry of Amino Acids Peptides and Proteins*, Weinstein Ed., Marcel Dekker, New York, 1984, pp. 267–357.

Spatola et al., Structure–Activity Relationships of Enkephalins Containing Serially Replaced Thiomethylene Amide Bond Surrogates, *Life Sciences*, 1982, vol. 38, pp. 1243–1249.

Suitters et al., Differential Effect of Isotype on Efficacy of Anti–Tumor Necrosis Factor α Chimeric Antibodies in Experimental Septic Shock, *J. Exp. Med.*, 1994, vol. 24, pp. 849–856.

Tak et al., Decrease in Cellularity and Expression of Adhesion Molecules by Anti–Tumor Necrosis Factor α Monoclonal Antibody Treatment in Patients with Rheumatoid Arthritis, *Arthritis & Rheumat.*, 1996, vol. 39, pp. 1077–1081.

Tam et al., Improved Synthesis of 4–(Boc–aminoacyloxymethyl)–phenylacetic Acids for use in Solid Phase Peptide Synthesis, *Synthesis*, Dec. 1979, pp. 955–957.

(List continued on next page.)

*Primary Examiner*—John Ulm
(74) *Attorney, Agent, or Firm*—Woodcock Washburn Kurtz Mackiewicz & Norris LLP

(57) ABSTRACT

The present invention relates to peptides and peptide analogues designed from a binding loop of a member of the tumor necrosis factor receptor (TNF-R) superfamily. In particular, it relates to cyclic peptides and peptide analogues designed from a binding loop of TNF-R which inhibit TNF binding to its cellular receptors, and methods of making and using such compounds to inhibit the biological activities of TNF.

21 Claims, 9 Drawing Sheets

OTHER PUBLICATIONS

Figure 2:
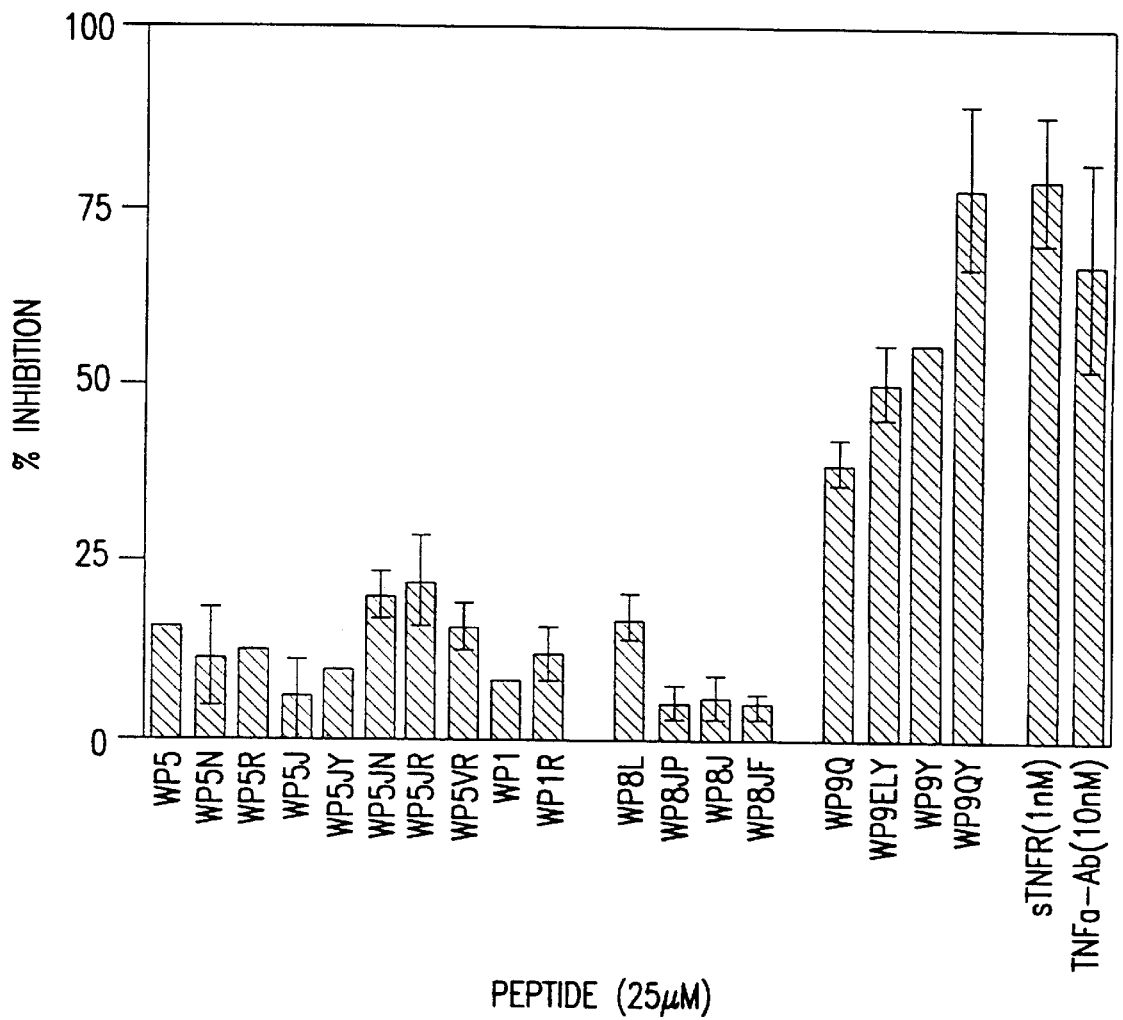

Walker et al., Inhibition of Immunoreactive Tumor Necrosis Factor–α by a Chimeric Antibody in Patients Infected with Human Inmmunodeficienty Virus Type 1, *J. Infect. Dis.*, 1996, vol. 174, pp. 63–68.

Williams et al., Anti–Tumor Necrosis Factor Amerliorates Joint Disease in Murine Collagen–Induced Arthritis, *Proc. Natl. Acad. Sci.*, 1992, vol. 89, pp. 9784–9788.

Williams et al., Successful Therapy of Collagen–induced Arthritis with TNF Receptor–IgG Fusion Protein and Combination with Anti–CD4, *Immunology*, 1995, vol. 84, pp. 433–439.

Zhang et al. Synthetic CD4 Exocyclic Inhibit Binding of Human Immunodeficiency Virus Type 1 Envelope to CD4 and Virus Replication in T Lmphocytes, *Nature Biotech*, 1997, vol. 15, p.150–154.

Zhang et al. Synthetic CD4 Exocyclic Peptides Antagonize CD4 Holoreceptor Binding and T Cell Activation, *Nature Biotech*, 1996, vol. 14, pp. 472–475.

|            | 70         80         90        100        110        120        130        140 |
|------------|---|
| TNF-R p55 | DCRECESGSFTASENHLRHCLSCSK.. CRKEMGQVEISS CTVDRDTV CGCRKNQYRHYWSENLFQ. C FN CSLCLNG.... T |
| TNF-R p75 | VCDSCEDSTYTQLWNWVPECLSCGSRC SSDQVE...TQA CTREQNRI CTCRPGWYCALSKQEGCRL C AP LRKCRPGFGV A |
| TNF-R rp | VCATCAENSYNEHWNYL..TICQLCRP CDPVMGLEEIAP CTSKRKTQ CRCQPGMFCAAWALE.CTH C EL LSDCPPGTEA E |
| NGF-R p75 | .CEPCLDSVIFSDVVSATEPCKPCTEC VGLQSMSAP... CVEADDAV CRCAYGYYQDETTGRCEAC R VC EAGSGLVFSC Q |
| CD27 | QCDPCIPGVSFS...PDHHTRPHCESC RHCNSGLLVRN. CTITANAE CACRNGW............ .........QC R |
| CD30(proximal) | CRKQCEPDYYLDEADRCTACVTCSRD. ......DLVEKTP CAWNSSRV CECRPGMFCSTSAVNSCAR C FF HSVCPAGMIV K |
| CD30(distal) | CRKQCEPDYYLDEAGRCTACVSCSRD. ......DLVEKTP CAWNSSRT CECRPGMICATSATNSCAR C VP YPICAAETVT K |
| CD40 | ECLPCGESEFLDTWNR..ETHCHQHKY CDPNLGLRVQQK GTSETDTI CTCEEGWHCT...SEACES C VL HRSCSPGFGV K |
| Fas | DCVPCQEGKEYTDKAHF.....SSK.. CRR............ ............ ............CRLQDEGHGL E |
| ox40 | .CRPC.GPGFYNDVVSS.KPCKPCTWC .NLRSGSERKQL CTATQDTV CR.............. .........Q RAGTQPLDSY . |
| 4-1BB | .CSPCPPNSF......SSAGGQRTCDIC RQCKGVFRTRKE CSSTSNAE CDCTPGFH.....CLGAGC S MC EQDCKQGQEL T |

FIG.1

FIG. 8A

IP/WB
αIRS-1/PY-20

| Insulin (100nM) | − | + | + | + | + | + | + | + | + |
|---|---|---|---|---|---|---|---|---|---|
| TNFα (50ng/ml) | − | − | − | − | − | + | + | + | + |
| WP9QY (μM) | 75 | 25 | 7.5 | 2.5 | − | − | 75 | 25 | 7.5 | 2.5 |

FIG. 8B

αIRS-1/αIRS-1

| Insulin (100nM) | + | + | + | + | + | + | + | + | + | − |
|---|---|---|---|---|---|---|---|---|---|---|
| TNFα (50ng/ml) | − | − | − | − | − | + | + | + | + | − |
| WP9QY (μM) | 75 | 25 | 7.5 | 2.5 | − | − | 75 | 25 | 7.5 | 2.5 |

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 74 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:1:

```
Asp Cys Arg Glu Cys Glu Ser Gly Ser Phe Thr Ala Ser Glu Asn His
 1               5                  10                  15

Leu Arg His Cys Leu Ser Cys Ser Lys Cys Arg Lys Glu Met Gly Gln
                20                  25                  30

Val Glu Ile Ser Ser Cys Thr Val Asp Arg Asp Thr Val Cys Gly Cys
            35                  40                  45

Arg Lys Asn Gln Tyr Arg His Tyr Trp Ser Glu Asn Leu Phe Gln Cys
        50                  55                  60

Phe Asn Cys Ser Leu Cys Leu Asn Gly Thr
65                  70
```

(2) INFORMATION FOR SEQ ID NO:2:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:2:

```
Val Cys Asp Ser Cys Glu Asp Ser Thr Tyr Thr Gln Leu Trp Asn Trp
 1               5                  10                  15

Val Pro Glu Cys Leu Ser Cys Gly Ser Arg Cys Ser Ser Asp Gln Val
                20                  25                  30

Glu Thr Gln Ala Cys Thr Arg Glu Gln Asn Arg Ile Cys Thr Cys Arg
            35                  40                  45

Pro Gly Trp Tyr Cys Ala Leu Ser Lys Gln Gly Gly Cys Arg Leu Cys
    50                  55                  60

Ala Pro Leu Arg Lys Cys Arg Pro Gly Phe Gly Val Ala
65                  70                  75
```

(2) INFORMATION FOR SEQ ID NO:3:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

```
Val Cys Ala Thr Cys Ala Glu Asn Ser Tyr Asn Glu His Trp Asn Tyr
 1               5                  10                  15

Leu Thr Ile Cys Gln Leu Cys Arg Pro Cys Asp Pro Val Met Gly Leu
                20                  25                  30

Glu Glu Ile Ala Pro Cys Thr Ser Lys Arg Lys Thr Gln Cys Arg Cys
            35                  40                  45

Gln Pro Gly Met Phe Cys Ala Ala Trp Ala Leu Glu Cys Thr His Cys
    50                  55                  60

Glu Leu Leu Ser Asp Cys Pro Pro Gly Thr Glu Ala Glu
65                  70                  75
```

(2) INFORMATION FOR SEQ ID NO:4:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

```
Cys Glu Pro Cys Leu Asp Ser Val Thr Phe Ser Asp Val Val Ser Ala
 1               5                  10                  15

Thr Glu Pro Cys Lys Pro Cys Thr Glu Cys Val Gly Leu Gln Ser Met
                20                  25                  30

Ser Ala Pro Cys Val Glu Ala Asp Ala Val Cys Arg Cys Ala Tyr
            35                  40                  45

Gly Tyr Tyr Gln Asp Glu Thr Thr Gly Arg Cys Glu Ala Cys Arg Val
```

```
                50                  55                  60
Cys Glu Ala Gly Ser Gly Leu Val Phe Ser Cys Gln
 65                  70                  75
```

(2) INFORMATION FOR SEQ ID NO:5:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

```
Gln Cys Asp Pro Cys Ile Pro Gly Val Ser Phe Ser Pro Asp His His
 1               5                  10                  15

Thr Arg Pro His Cys Glu Ser Cys Arg His Cys Asn Ser Gly Leu Leu
                20                  25                  30

Val Arg Asn Cys Thr Ile Thr Ala Asn Ala Glu Cys Ala Cys Arg Asn
                35                  40                  45

Gly Trp Gln Cys Arg
                50
```

(2) INFORMATION FOR SEQ ID NO:6:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

```
Cys Arg Lys Gln Cys Glu Pro Asp Tyr Tyr Leu Asp Glu Ala Asp Arg
 1               5                  10                  15

Cys Thr Ala Cys Val Thr Cys Ser Arg Asp Asp Leu Val Glu Lys Thr
                20                  25                  30

Pro Cys Ala Trp Asn Ser Ser Arg Val Cys Glu Cys Arg Pro Gly Met
                35                  40                  45

Phe Cys Ser Thr Ser Ala Val Asn Ser Cys Ala Arg Cys Phe Phe His
       50                  55                  60

Ser Val Cys Pro Ala Gly Met Ile Val Lys
 65                  70
```

(2) INFORMATION FOR SEQ ID NO:7:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:7:

```
Cys Arg Lys Gln Cys Glu Pro Asp Tyr Tyr Leu Asp Glu Ala Gly Arg
 1               5                  10                  15

Cys Thr Ala Cys Val Ser Cys Ser Arg Asp Asp Leu Val Glu Lys Thr
                20                  25                  30

Pro Cys Ala Trp Asn Ser Ser Arg Thr Cys Glu Cys Arg Pro Gly Met
                35                  40                  45
```

```
Ile Cys Ala Thr Ser Ala Thr Asn Ser Cys Ala Arg Cys Val Pro Tyr
    50                  55                  60

Pro Ile Cys Ala Ala Glu Thr Val Thr Lys
65                  70
```

(2) INFORMATION FOR SEQ ID NO:8:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

```
Glu Cys Leu Pro Cys Gly Glu Ser Glu Phe Leu Asp Thr Trp Asn Arg
1               5                   10                  15

Glu Thr His Cys His Gln His Lys Tyr Cys Asp Pro Asn Leu Gly Leu
                20                  25                  30

Arg Val Gln Gln Lys Gly Thr Ser Glu Thr Asp Thr Ile Cys Thr Cys
            35                  40                  45

Glu Glu Gly Trp His Cys Thr Ser Glu Ala Cys Glu Ser Cys Val Leu
    50                  55                  60

His Arg Ser Cys Ser Pro Gly Phe Gly Val Lys
65                  70                  75
```

(2) INFORMATION FOR SEQ ID NO:9:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

```
Asp Cys Val Pro Cys Gln Glu Gly Lys Glu Tyr Thr Asp Lys Ala His
1               5                   10                  15

Phe Ser Ser Lys Cys Arg Arg Cys Arg Leu Cys Asp Glu Gly His Gly
                20                  25                  30

Leu Glu
```

(2) INFORMATION FOR SEQ ID NO:10:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

```
Cys Arg Pro Cys Gly Pro Gly Phe Tyr Asn Asp Val Val Ser Ser Lys
1               5                   10                  15

Pro Cys Lys Pro Cys Thr Trp Cys Asn Leu Arg Ser Gly Ser Glu Arg
                20                  25                  30

Lys Gln Leu Cys Thr Ala Thr Gln Asp Thr Val Cys Arg Cys Arg Ala
            35                  40                  45

Gly Thr Gln Pro Leu Asp Ser Tyr
```

50                  55

(2) INFORMATION FOR SEQ ID NO:11:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

Cys Ser Pro Cys Pro Pro Asn Ser Phe Ser Ser Ala Gly Gly Gln Arg
 1               5                  10                  15

Thr Cys Asp Ile Cys Arg Gln Cys Lys Gly Val Phe Arg Thr Arg Lys
            20                  25                  30

Glu Cys Ser Ser Thr Ser Asn Ala Glu Cys Asp Cys Thr Pro Gly Phe
        35                  40                  45

His Cys Leu Gly Ala Gly Cys Ser Met Cys Glu Gln Asp Cys Lys Gln
    50                  55                  60

Gly Gln Glu Leu Thr
65

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:12:

Tyr Cys Glu Leu Ser Gln Tyr Leu Cys Tyr
 1               5                  10

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:13:

Tyr Cys Trp Ser Gln Asn Leu Cys Tyr
 1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:14:

Tyr Cys Trp Ser Gln Asn Tyr Cys Tyr
 1               5

```
(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

Tyr Cys Trp Ser Gln Tyr Leu Cys Tyr
 1               5

(2) INFORMATION FOR SEQ ID NO:16:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

Tyr Cys Phe Thr Ala Ser Glu Asn His Cys Tyr
 1               5                  10

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

Tyr Cys Phe Thr Asn Ser Glu Asn His Cys Tyr
 1               5                  10

(2) INFORMATION FOR SEQ ID NO:18:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

Tyr Cys Phe Thr Arg Ser Glu Asn His Cys Tyr
 1               5                  10

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

Phe Cys Ala Ser Glu Asn His Cys Tyr
 1               5
```

(2) INFORMATION FOR SEQ ID NO:20:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:20:

Tyr Cys Ala Ser Glu Asn His Cys Tyr
1           5

(2) INFORMATION FOR SEQ ID NO:21:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:21:

Phe Cys Asn Ser Glu Asn His Cys Tyr
1           5

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:22:

Phe Cys Asn Ser Glu Asn Arg Cys Tyr
1           5

(2) INFORMATION FOR SEQ ID NO:23:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:23:

Phe Cys Asn Ser Val Glu Asn Arg Cys Tyr
1           5           10

(2) INFORMATION FOR SEQ ID NO:24:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:24:

Tyr Cys Arg Lys Glu Leu Gly Gln Val Cys Tyr
1           5           10

```
(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:25:

Tyr Cys Lys Glu Pro Gly Gln Cys Tyr
 1               5

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

Tyr Cys Arg Lys Glu Met Gly Cys Tyr
 1               5

(2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:27:

Phe Cys Arg Lys Glu Met Gly Cys Tyr
 1               5
```

PEPTIDES AND PEPTIDE ANALOGUES DESIGNED FROM BINDING SITES OF TUMOR NECROSIS FACTOR RECEPTOR SUPERFAMILY AND THEIR USES

1. INTRODUCTION

The present invention relates to peptides and peptide analogues designed from a binding loop of a member of the tumor necrosis factor receptor (TNF-R) superfamily, which is involved in binding interactions with its ligand. In particular, it relates to cyclic peptides and peptide analogues designed from three specific binding loops in domains 2 and 3 of TNF-R which inhibit tumor necrosis factor (TNF) binding to its cellular receptors, methods of designing similar peptides and peptide analogues, and methods of using such compounds to inhibit the biological activities of TNF, thereby antagonizing its undesirable clinical effects.

2. BACKGROUND OF THE INVENTION

2.1. Tumor Necrosis Factor and its Pathophysiology

TNF was originally discovered as a molecule which caused hemorrhagic necrosis of mouse tumors (Carswell et al., 1975, Proc. Natl. Acad. Sci. U.S.A. 72:3666). A second line of investigation of a serum protein known as "cachectin", thought to be responsible for the condition of cachexia, led to the eventual discovery that cachectin was identical to TNF (Beutler et al., 1989, Annu. Rev. Immunol. 7:625). TNF has now been established as a broadly active inflammatory mediator involved in diverse clinical conditions.

TNF/cachectin was renamed as TNF-α, and a structurally and functionally related protein previously known as lymphotoxin (LT) was referred as TNF-β (Vassalli, 1992, Annu. Rev. Immunol. 10:411). Both molecules are active as homotrimers and mediate similar biological effects by binding to the same two cellular receptors of 55 kD (p55 or complex I) and 75 kD (p75) molecular weight (Smith et al., 1990, Science 248:1019; Schall et al., 1990, Cell 61:361). An LT heterotrimer was later discovered, which engaged a third receptor known as TNF-R related protein (rp), but it is not capable of binding to TNF-R p55 and p75 (Browning et al., 1993, Cell 72:847). This LT has been named as LT-β, and the LT homotrimer (or TNF-β) is also referred to as LT-α. Structural comparison of the three TNF-R with several other cell surface receptors has resulted in the classification of these receptors into the TNF-R superfamily (Gruss and Dower, 1995, Cytokines and Mol. Ther. 1:75).

TNF-α is a 17 kD molecular weight protein produced by several cell types, particularly activated macrophages. Since TNF-R is expressed by numerous cell populations, TNF induces a wide variety of cellular responses, many of which result in deleterious consequences. For example, TNF induces cachexia which is a condition resulting from loss of fat and whole body protein depletion, accompanied by insufficient food intake due to anorexia. Cachexia is commonly seen in cancer patients, and it has also been observed in patients with acquired immunodeficiency syndrome (AIDS).

In addition, injection of high doses of TNF in animals produces most of the symptoms of septic shock. TNF has also been shown to play a role in autoimmune diseases such as multiple sclerosis and rheumatoid arthritis, hypersensitivity, immune complex diseases and graft versus host disease as well as transplantation rejection. The involvement of TNF has even been implicated in malaria and lung fibrosis.

2.2. Treatment of TNF-Associated Disorders

Methods for neutralizing the adverse effects of TNF have focused on the use of anti-TNF antibodies and soluble TNF-R. In animal models, treatment of TNF-associated inflammatory disorders with antibodies specific for TNF has shown therapeutic efficacy (Williams et al., 1992, Proc. Natl. Acad. Sci. U.S.A. 89:9784; Baker et al., 1994, Eur. J. Immunol. 24:2040; Suitters et al., 1994, J. Exp. Med. 179:849). Chimeric forms of anti-TNF antibodies have been constructed for use in human clinical trials (Lorenz et al., 1996, J. Immunol. 156:1646; Walker et al., 1996, J. Infect. Dis. 174:63; Tak et al., 1996, Arthritis Rheumat. 39:1077). Additionally, soluble TNF-R fusion proteins have been introduced as TNF-antagonists in human patients (Peppel et al., 1991, J. Exp. Med. 174:1483; Williams et al., 1995, Immunol. 84:433; Baumgartner et al., 1996, Arthritis Rheumat. 39(Suppl.) S74).

While the aforementioned approaches have shown some effectiveness in certain disease conditions, anti-TNF antibodies and soluble TNF-R both suffer from common limitations of macromolecules such as poor bioavailability and stability, induction of immune reactions and ineffective tissue penetration. Thus, there remains a need for improved therapeutic compounds for antagonizing the undesirable effects of TNF.

3. SUMMARY OF THE INVENTION

The present invention relates to peptides and peptide analogues designed from a binding loop of a TNF-R superfamily member. In particular, it relates to peptides and peptide analogues designed from three binding loops of TNF-R. More specifically, the invention relates to peptides and peptide analogues which interfere with the binding interactions between TNF and TNF-R, methods of designing additional peptides and peptide analogues exhibiting inhibitory activities, and methods of using such compounds and pharmaceutical compositions thereof to antagonize the undesirable biological activities of TNF in vivo, as well as methods of using the compounds to detect the presence of TNF in a sample and for inhibiting TNF activities in vitro.

The invention is based, in part, on the Applicants' discovery that peptides designed from three binding loops of TNF-R p55 inhibited TNF-α binding to TNF-R. Such peptides were generated on the basis of the amino acid sequences that form the specific binding loops. Cys residues were added to the peptides to enable their cyclization by formation of disulfide bridges, and hydrophobic aromatic residues were added to their termini to enhance structural stability. Among the peptides that competitively inhibited the binding of TNF-α to its cognate receptor, peptides designed from loop 1 of domain 3 of TNF-R were the most effective.

Generally, a compound of the present invention is a cyclic peptide or peptide analogue which is modified at its termini with hydrophobic moieties. In embodiments wherein the compound is a peptide, the peptide corresponds in primary sequence to a binding loop of a member of the TNF-R superfamily or a portion thereof. In a preferred embodiment, the peptide corresponds in primary sequence to a binding loop of TNF-R p55 or a portion thereof. In certain embodiments, one or more amino acid residues within the peptide are substituted with other amino acid residues. Typically, such amino acid substitutions are conservative, i.e., the amino acid residues are replaced with other amino acid residues having similar physical and/or chemical properties. In embodiments wherein the compound is a peptide analogue, the analogue is obtained by replacing at least one amide linkage in the peptide with a substituted amide or an isostere of amide.

In an illustrative embodiment, a compound of the invention has the following formula:

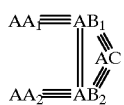

(I)

wherein:

AC is a peptide of 3–18 amino acid residues which corresponds in primary sequence to a binding loop of a TNF-R superfamily member, and which may optionally contain one or more conservative amino acid substitutions, or an analogue thereof wherein at least one amide linkage is replaced with a substituted amide or an isostere of amide;

$AB_1$ is a moiety having a first functional group capable of forming a covalent linkage with one terminus of AC, a second functional group capable of forming a covalent linkage with $AB_2$ and a third functional group capable of forming a covalent linkage with $AA_1$;

$AB_2$ is a moiety having a first functional group capable of forming a covalent linkage with the second terminus of AC, a second functional group capable of forming a covalent linkage with $AB_1$ and a third functional group capable of forming a covalent linkage with $AA_2$;

$AA_1$ is a moiety having hydrophobic properties and a functional group capable of forming a covalent linkage with the third functional group of $AB_1$;

AA2 is a moiety having hydrophobic properties and a functional group capable of forming a covalent linkage with the third functional group of $AB_2$;

"=" is a covalent linkage; and

"≡" is a covalent linkage.

In a preferred embodiment of the compounds of formula (I) AC is a peptide which corresponds in primary sequence to a binding loop of TNF-R p55 and which optionally may contain one or more conservative amino acid substitutions, or an analogue thereof. In a particularly preferred embodiment, the peptides and peptide analogues specifically inhibit the binding of TNF to its cellular receptors. Therefore, such compounds are useful in antagonizing the undesirable biological activities of TNF. In that connection, a wide variety of specific uses are encompassed by the invention, including but not limited to, treatment of TNF-associated pathological conditions such as acute and chronic inflammatory responses, septic shock, cachexia, autoimmunity, graft-versus-host disease, skin allergic reactions, immune complex disease, transplantation rejection and malaria.

4. BRIEF DESCRIPTION OF THE DRAWINGS

FIG. 1. Sequence alignment of amino acids in certain extracellular Cys-rich domains of TNF-R superfamily members: TNF-R p55 (SEQ ID NO:1), TNF-R p75 (SEQ ID NO:2), TNF-R-rp (SEQ ID NO: 3), NGF-R p75 (SEQ ID NO:4), CD27 (SEQ ID NO:5), CD30 (proximal) (SEQ ID NO:6), CD30 (distal) (SEQ ID NO:7), CD40 (SEQ ID NO:8), Fas antigen (SEQ ID NO:9), OX40 (SEQ ID NO:10), and 4-IBB (SEQ ID NO:11).

FIG. 2. Inhibition of radiolabeled-TNF-α interaction with TNF-R. In a competitive radioreceptor assay, $^{125}$I-labelled TNF was preincubated with a peptide followed by binding to immobilized TNF-R. The peptides were compared at 25 μM for their ability to inhibit the binding of TNF-α (10 nM) to 1 nM of TNF-R-IgG chimeric protein.

Figure 3:
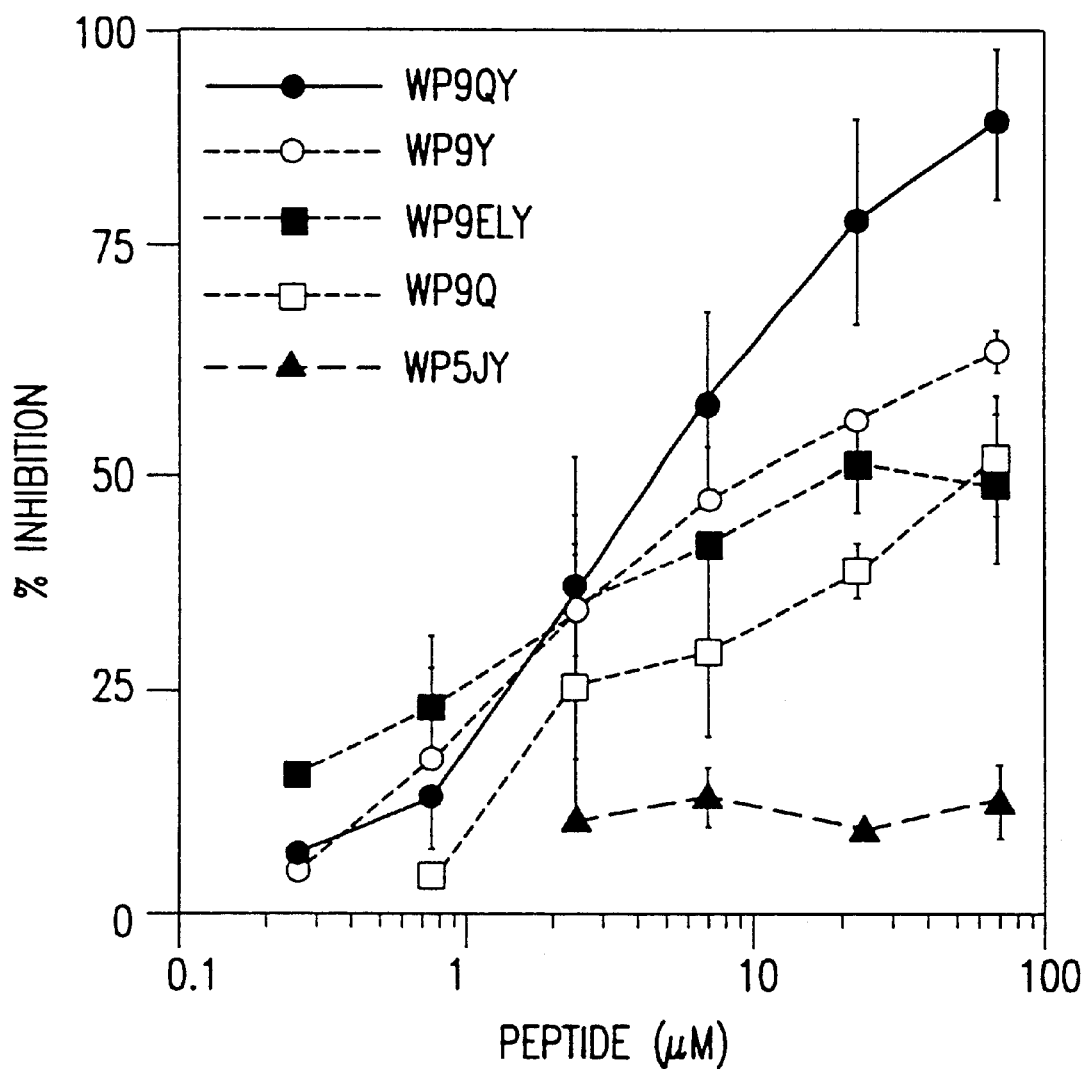

FIG. 3. Inhibition of radiolabeled-TNF-α interaction with TNF-R in a dose-response assay. In a competitive radioreceptor assay, TNF-α binding to immobilized TNF-R-chimeric protein was inhibited in the presence of several WP9 series peptides in a defined dose range. The results represent the means and standard deviations from three independent experiments.

Figure 4:
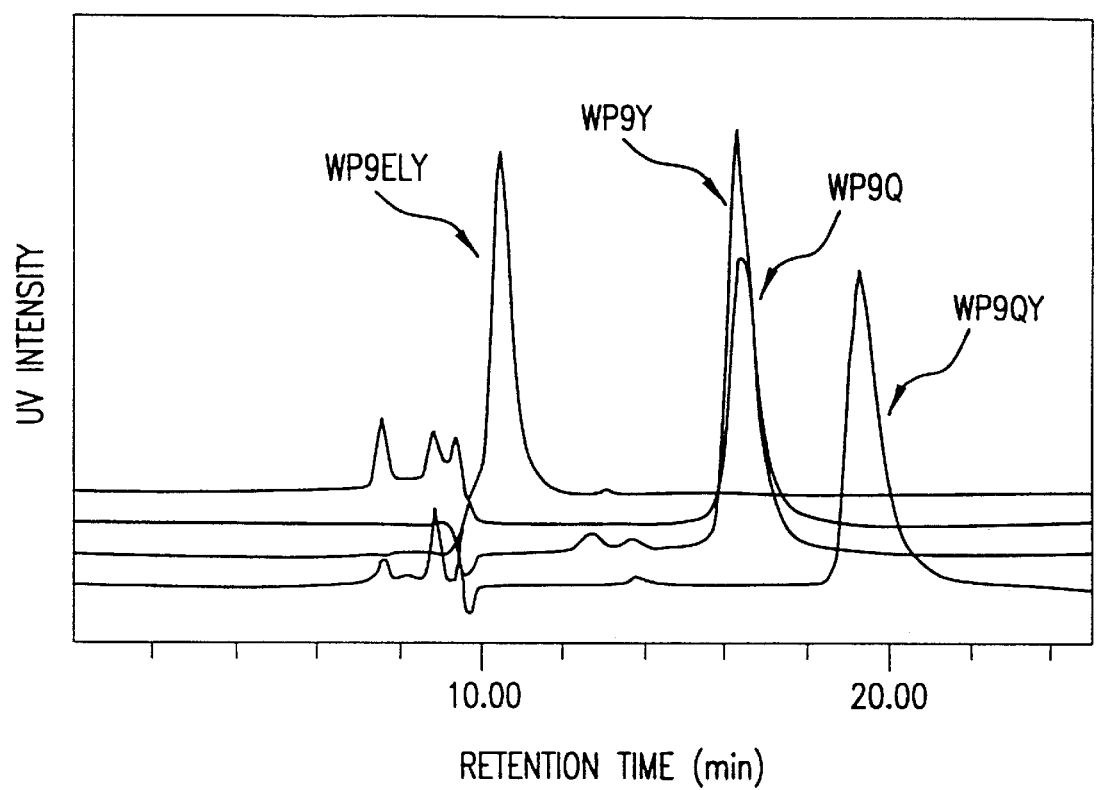

FIG. 4. Size exclusion HPLC profiles of exocyclic peptides. Each peptide (4 mg) was eluted from Protein-Pak 60 column with 0.1M phosphate buffer at pH 7.0 at a flow rate of 1 ml/min. and their UV was monitored at 214 nm.

Figure 5:
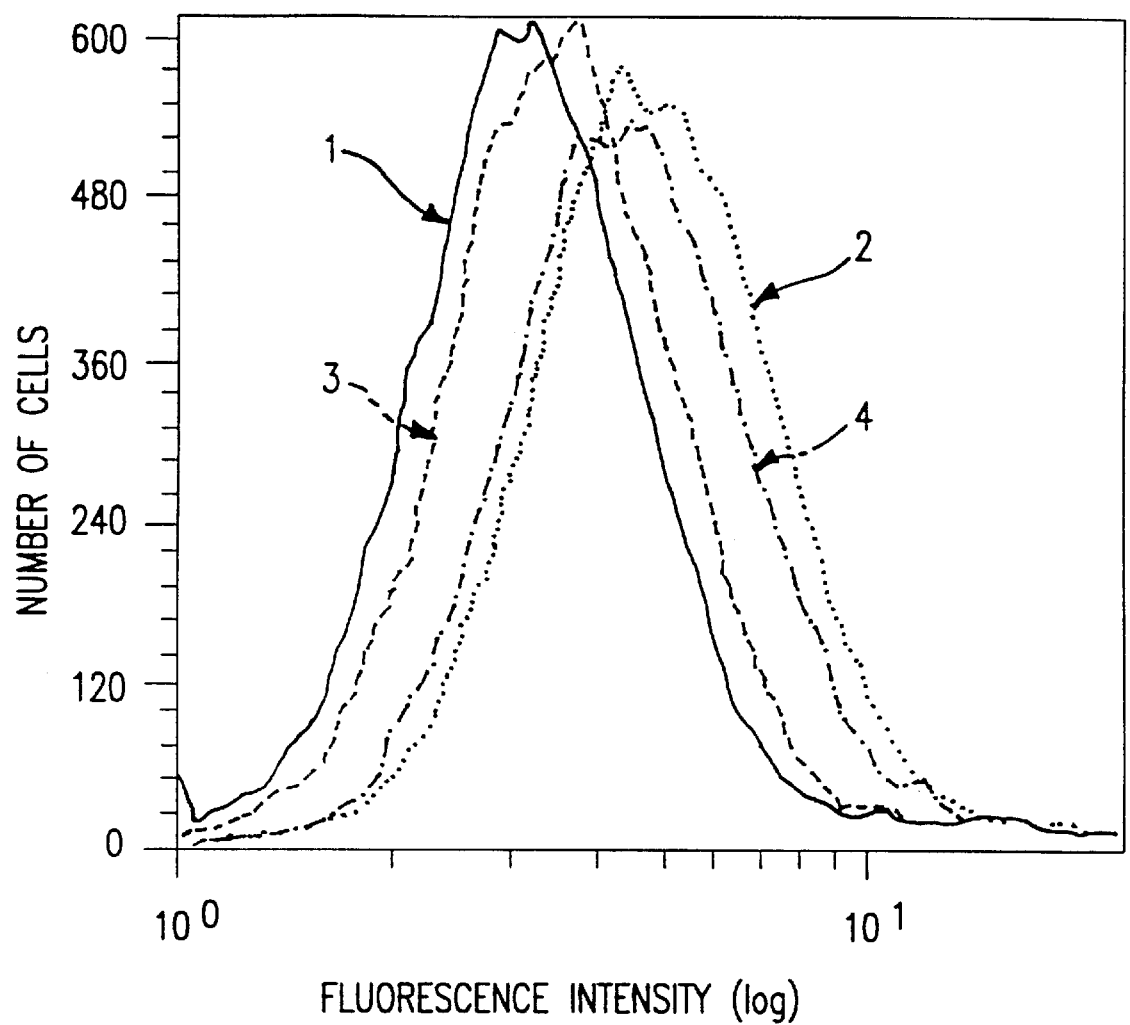

FIG. 5. FAC analysis of TNF-α binding to cellular receptors in the presence of WP9QY peptide. 1=U937 cells stained with fluorescein-conjugated secondary antibody. 2=U937 cells stained with an anti-TNF receptor antibody (htr-9) and secondary antibody. 3=U937 cells stained with anti-TNF-R antibody in the presence of TNF-α and secondary antibody. 4=U937 cells stained with an anti-TNF receptor antibody (htr-9) and TNF-α preincubated with 250 μM of WP9QY peptide.

Figure 6:
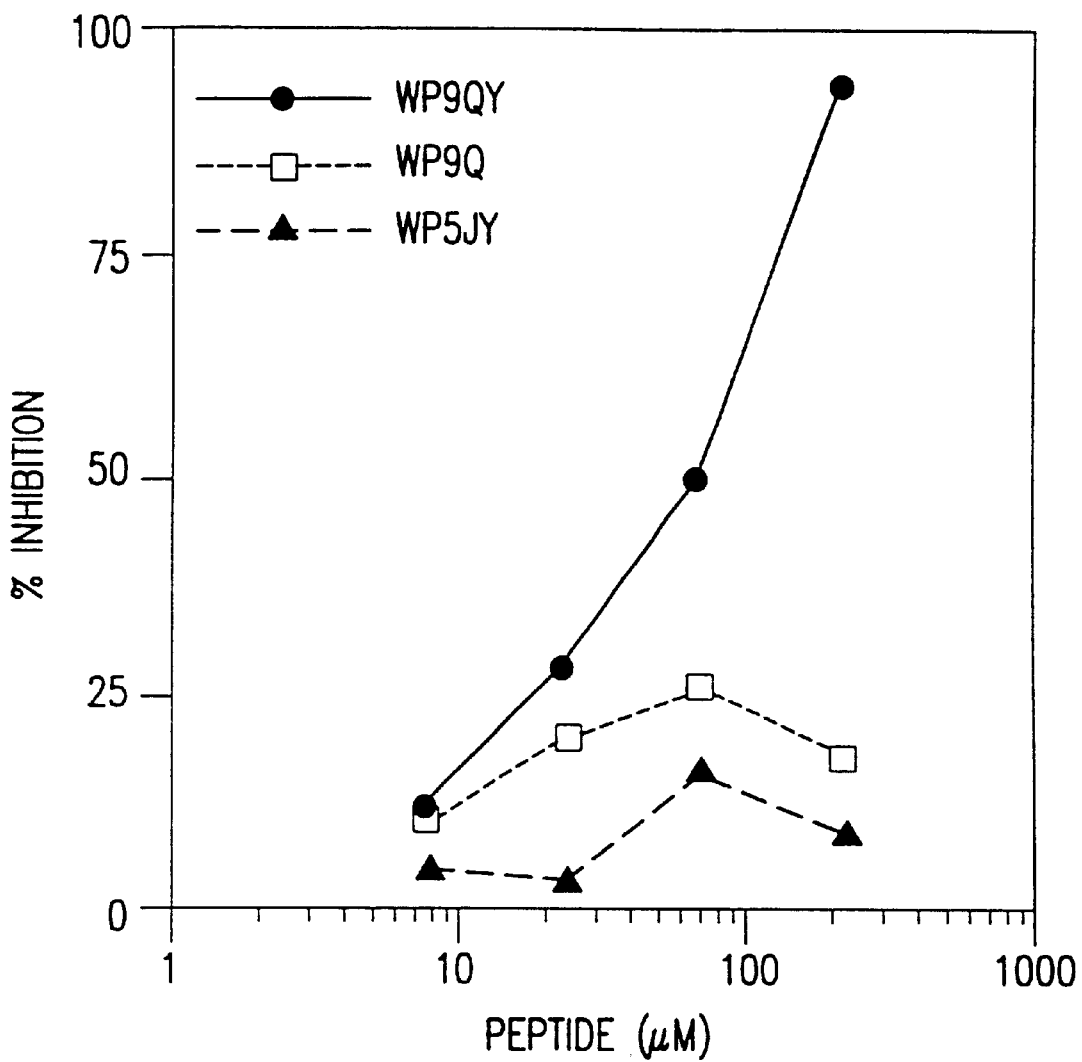

FIG. 6. FAC analysis of TNF-α binding to cellular receptors in the presence of one of three peptides derived from TNF-R. TNF-α binding to U937 cells were inhibited by each peptide in a dose-dependent manner. —●—=WP9QY peptide; - - - □ - - - =WP9Q peptide; - - - ▲ - - - =WP5JY peptide. The results represent the means from two independent experiments.

Figure 7:
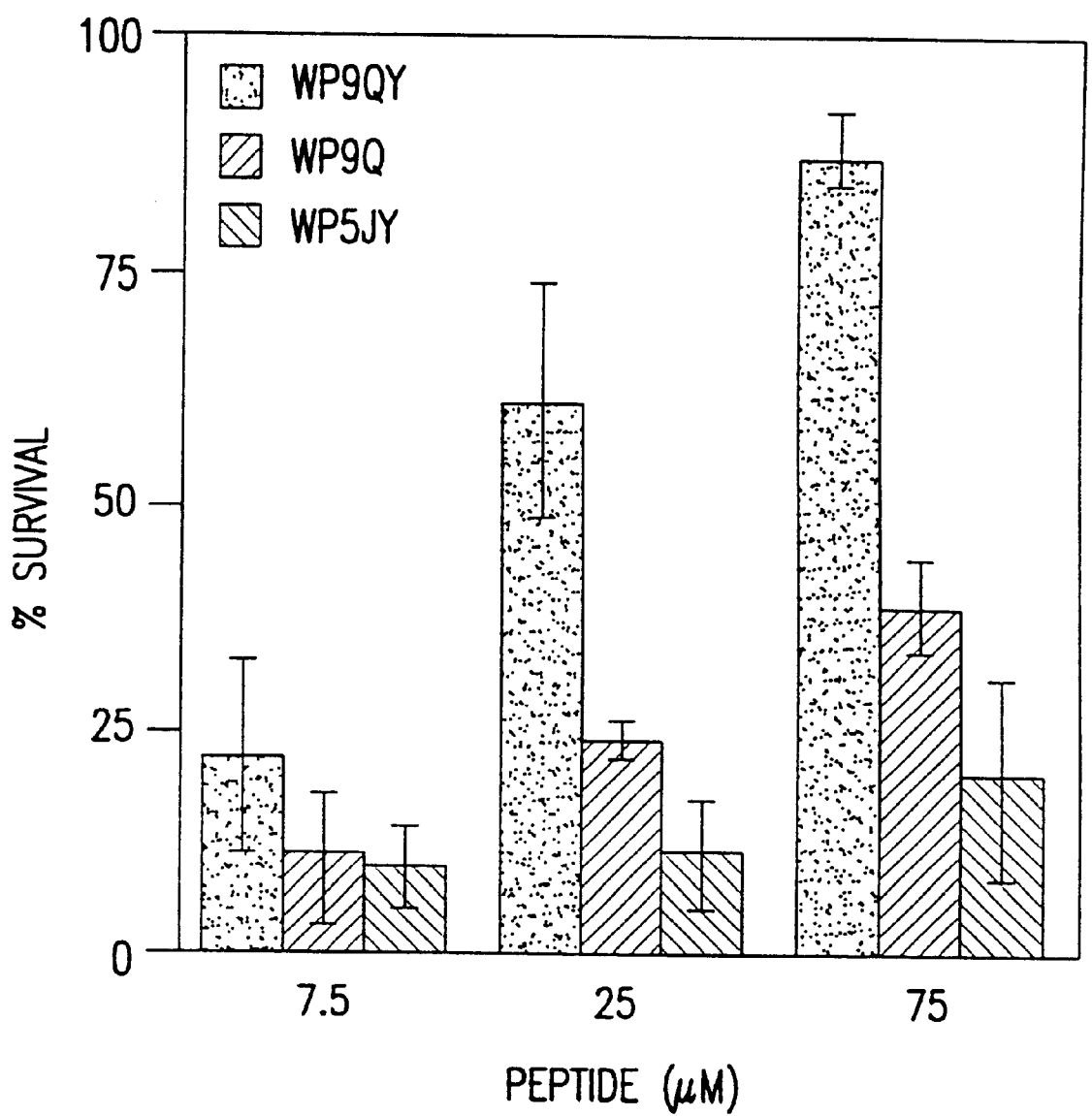

FIG. 7. Inhibition of TNF-α-induced cytolysis of L929 cells by peptides derived from TNF-R. Absorbance with 1 μg/ml of ACT-D alone and with ACT-D plus 50 pg/ml of TNF-α are referred to as 100% survival and 100% cytotoxicity, respectively. The results indicate the means and standard deviations from three independent experiments.

FIGS. 8A & B Inhibition of TNF-α-induced insulin resistance by WP9QY peptide. Differentiated 3T3-L1 cells were stimulated with insulin, and Tyr phosphylated IRS-1 was assayed. Certain samples were also treated with TNF-α which inhibited Tyr phosphorylation of IRS-1. Preincubation of TNF-α with WP9QY peptide restored Tyr phosphorylation of IRS-1 in response to insulin. FIG. 8A shows the results of Western blot with an anti-phosphorylated Tyr antibody after immunoprecipitation with an anti-IRS-1 antiserum. FIG. 8B shows the results of Western blot following immunoprecipitation with the same anti-IRS-1 antiserum.

Figure 9:
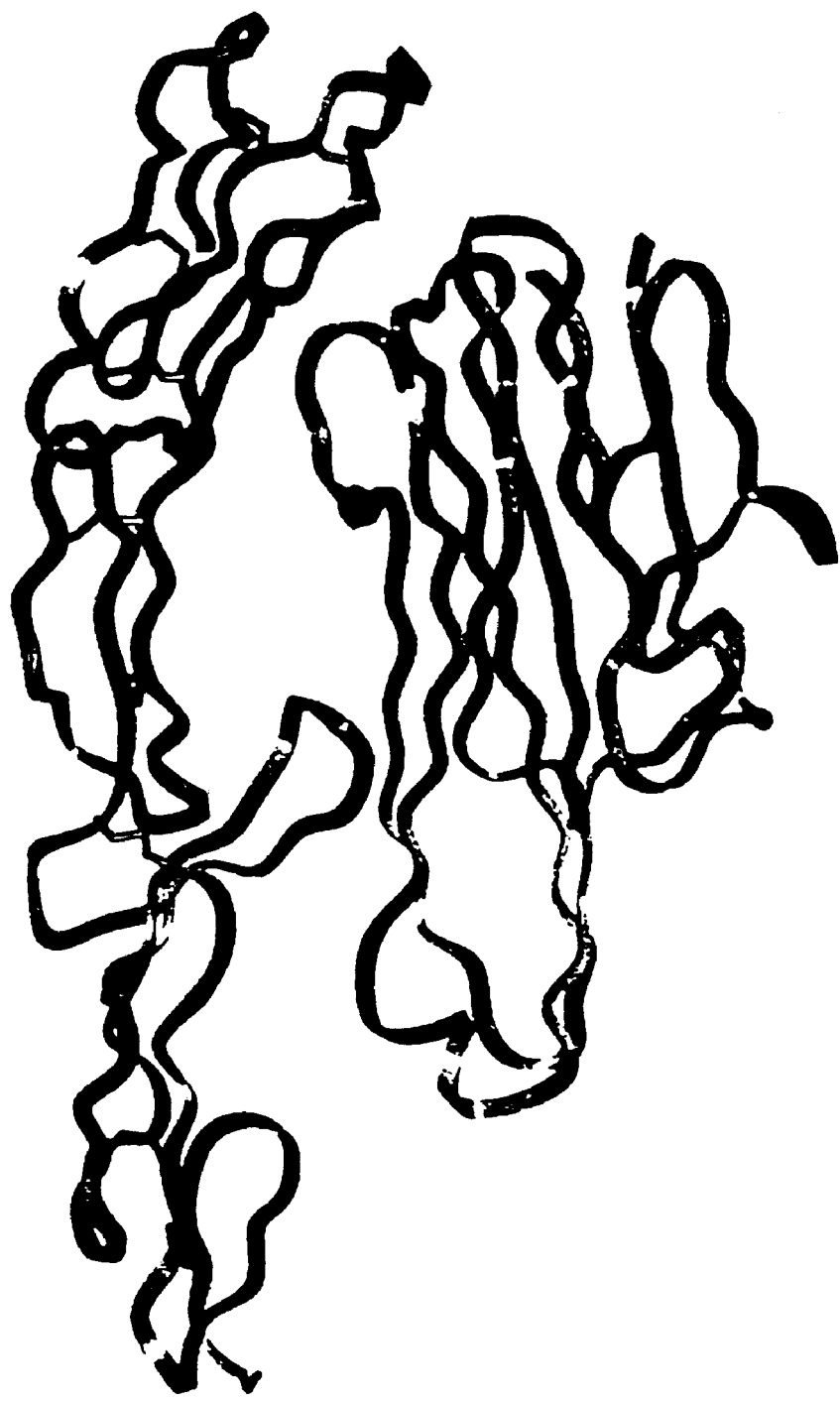

FIG. 9. Three dimensional structural view of the binding sites in TNF-R for TNF-α. Monomeric TNF-α is shown on the right and monomeric TNF-R is shown on the left with the binding site in loop 1 of domain 3 shown in darkened color.

5. DETAILED DESCRIPTION OF THE INVENTION

The present invention relates to cyclic peptides and peptide analogues which inhibit the binding interactions between a TNF-R superfamily member and its ligand. Although the specific procedures and methods described herein are exemplified using several specific peptides derived from TNF-R p55, they are merely illustrative for the practice of the invention. Analogous procedures and techniques, as well as functionally equivalent peptides and peptide analogues, as will be apparent to those of skill in the art based on the detailed disclosure provided herein are also encompassed by the invention.

As used herein, the following terms shall have the following meanings:

"Alkyl:" refers to a saturated branched, straight chain or cyclic hydrocarbon group. Typical alkyl groups include, but are not limited to, methyl, ethyl, propyl, isopropyl, butyl, isobutyl, t-butyl, pentyl, isopentyl, hexyl, and the like. In preferred embodiments, the alkyl groups are ($C_1$–$C_6$) alkyl, with ($C_1$–$C_3$) being particularly preferred.

"Substituted Alkyl:" refers to an alkyl group wherein one or more hydrogen atoms are each independently replaced with other substituents.

"Alkenyl:" refers to an unsaturated branched, straight chain or cyclic hydrocarbon group having at least one carbon-carbon double bond. The group may be in either the cis or trans conformation about the double bond(s). Typical alkenyl groups include, but are not limited to, ethenyl, propenyl, isopropenyl, butenyl, isobutenyl, tert-butenyl, pentenyl, hexenyl and the like. In preferred embodiments, the alkenyl group is ($C_1$–$C_6$) alkenyl, with ($C_1$–$C_3$) being particularly preferred.

"Substituted Alkenyl:" refers to an alkenyl group wherein one or more hydrogen atoms are each independently replaced with other substituents.

"Alkynyl:" refers to an unsaturated branched, straight chain or cyclic hydrocarbon group having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is ($C_1$–$C_6$) alkynyl, with ($C_1$–$C_3$) being particularly preferred.

"Substituted Alkynyl:" refers to an alkynyl group wherein one or more hydrogen atoms are each independently replaced with other substituents.

"Alkoxy:" refers to an —OR group, where R is alkyl, alkenyl or alkynyl, as defined above.

"Aromatic moiety:" refers to a moiety having an unsaturated cyclic hydrocarbon group which has a conjugated (4n+2)π electron system. Typical aromatic moieties include, but are not limited to, benzene, naphthalene, anthracene, azulene, indacene, and the like. In preferred embodiments, the aromatic moiety contains 5–20 carbons in the ring system, with 5–10 carbon atoms being particularly preferred.

"Substituted Aromatic Moiety:" refers to an aromatic moiety wherein one or more hydrogen atoms are each independently replaced with other substituents.

"Heteroaromatic moiety:" refers to an aromatic moiety wherein one or more of the ring carbon atoms is replaced with another atom such as N, O or S. Typical heteroaromatic moieties include, but are not limited to, pyran, pyrazole, pyridine, pyrrole, pyrazine, pyridazine, pyrimidine, pyrrolizine, quinazoline, quinoline, quinolizine, quinoxaline, selenophene, thiophere, tellurophene, xanthene and the like.

"Substituted Heteroaromatic moiety:" refers to a heteroaromatic moiety wherein one or more hydrogen atoms are each independently replaced with other substituents.

5.1. The TNF-R Superfamily

TNF exerts its biological activities by binding to two TNF-R: p55 and p75. A comparison of these receptors with several other cell surface receptors revealed certain shared structural features that led to their classification as a superfamily (Beutler et al., 1994, *Science* 264:667). The TNF-R superfamily members possess characteristic extracellular Cys-rich domains, yet share only about 25% sequence homology. There are at least ten members in this superfamily, including: TNF-R p55 and p75, TNF-R related protein (rp), CD40, Fas antigen (CD95), low-affinity nerve growth factor receptor (p75), CD27, CD30, 4-1BB and OX40 (Beutler et al., 1994, *Ann. NY Acad. Sci.* pp. 118–133; Gruss and Dower, 1995, *Cytokines and Mol. Ther.* 1:75–105).

Loops and turns in many proteins have been shown to play functionally important roles in protein-protein interactions. In a specific embodiment illustrated by way of examples in Section 6, infra, cyclic peptides were designed from three binding loops of TNF-R p55 which inhibited the binding of TNF to its cellular receptors. In particular, peptides designed from loop 1 of domain 3 exhibited the strongest inhibitory activities. When a peptide designed from this binding loop was used in combination with peptides designed from two other loops, no further increase in inhibitory effects were observed, indicating that loop 1 of domain 3 is a dominant ligand binding site in TNF-R.

Based on this finding, corresponding regions of other TNF-R superfamily members from which inhibitory peptides and peptide analogues can be designed are readily identified by amino acid sequence alignment with the three specific binding sites of TNF-R p55 (FIG. 1). Since the dominant binding site of TNF-R p55 falls within amino acid residues #119 to 136, which sequence starts and ends with Cys, the same region in each TNF-R superfamily member may be used to design peptides and peptide analogues that are within the scope of the present invention. In cases where the regions do not start or end with Cys, the region may extend to the next Cys. For example, the corresponding region in Fas is deleted, and thus this region in Fas starts at residue #97 and ends with #143. In the case of NGF-R, the region ends at the Cys at position at 135. Additionally, residues 74–81 and 97–110 may also be used to design additional peptides and peptide analogues within the scope of the present invention. Such compounds are then cyclized and modified at their termini with hydrophobic moieties as described in greater detail in the sections below.

5.2. Peptides and Peptide Analogues Designed from Binding Loops of a TNF-R Superfamily Member Generally, a compound of the present invention is a cyclic peptide or peptide analogue. The peptide or peptide analogue is modified at its termini with hydrophobic moieties. In embodiments wherein the compound is a peptide, the peptide corresponds in primary sequence to a binding loop of a member of the TNF-R superfamily or a portion thereof. In a preferred embodiment, the peptide corresponds in primary sequence to a binding loop of TNF-R p55 or a portion thereof. In certain embodiments, one or more amino acid residues within the peptide are substituted with other amino acid residues. Typically, such amino acid substitutions are conservative, i.e., the amino acid residues are replaced with other amino acid residues having physical and/or chemical properties similar to the residues they are replacing. Preferably, conservative amino acid substitutions are those wherein an amino acid is replaced with another amino acid encompassed within the same designated class, as will be described more thoroughly below. In embodiments wherein the compound is a peptide analogue, the analogue is obtained by replacing at least one amide linkage in the peptide with a substituted amide or an isostere of amide.

In an illustrative embodiment, a compound of the invention has the following formula:

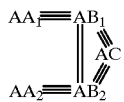

(I)

wherein:
- AC is a peptide of 3–18 amino acid residues, preferably 5–8 amino acid residues, which corresponds in primary sequence to a binding loop of a TNF-R and which may optionally contain conservative amino acid substitutions, or an analogue thereof wherein at least one amide linkage is replaced with a substituted amide or an isostere of amide;
- $AB_1$ is a moiety having a first functional group capable of forming a covalent linkage with one terminus of AC, a second functional group capable of forming a covalent linkage with $AB_2$ and a third functional group capable of forming a covalent linkage with $AA_1$;
- $AB_2$ is a moiety having a first functional group capable of forming a covalent linkage with the second terminus of AC, a second functional group capable of forming a covalent linkage with $AB_1$ and a third functional group capable of forming a covalent linkage with $AA_2$;
- $AA_1$ is a moiety having hydrophobic properties and a functional group capable of forming a covalent linkage with the third functional group of $AB_1$;
- $AA_2$ is a moiety having a hydrophobic properties and a functional group capable of forming a covalent linkage with the third functional group of $AB_2$;
- "=" is a covalent linkage; and
- "≡" is a covalent linkage.

More specifically, the compounds of the invention are illustrated by three specific embodiments having the following formulae:

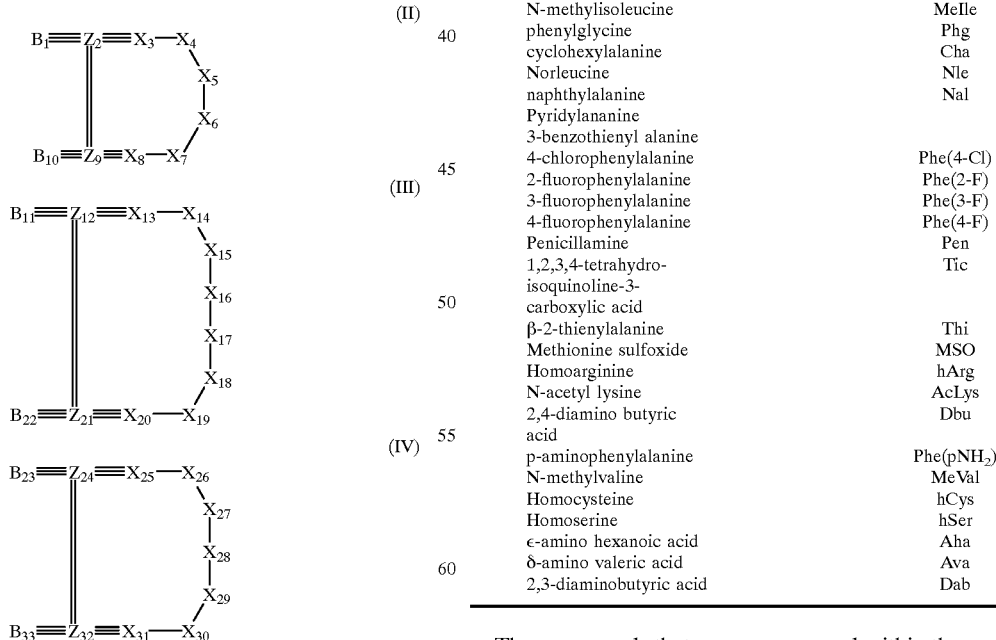

The designation $X_n$ in each case represents an amino acid at the specified position in the compound. Similarly, the designation $Z_n$ represents an amino acid or other moiety which is capable of forming covalent linkages with other $Z_n$, such as disulfide bridges.

The amino acid residues denoted by $X_n$ or $Z_n$ may be the genetically encoded L-amino acids, naturally occurring non-genetically encoded L-amino acids, synthetic L-amino acids or D-enantiomers of all of the above. The amino acid notations used herein for the twenty genetically encoded L-amino acids and common non-encoded amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-alanine | | bAla |
| 2,3-diaminopropionic acid | | Dpr |
| -α-aminoisobutyric acid | | Aib |
| N-methylglycine (sarcosine) | | MeGly |
| Ornithine | | Orn |
| Citrulline | | Cit |
| t-butylalanine | | t-BuA |
| t-butylglycine | | t-BuG |
| N-methylisoleucine | | MeIle |
| phenylglycine | | Phg |
| cyclohexylalanine | | Cha |
| Norleucine | | Nle |
| naphthylalanine | | Nal |
| Pyridylananine | | |
| 3-benzothienyl alanine | | |
| 4-chlorophenylalanine | | Phe(4-Cl) |
| 2-fluorophenylalanine | | Phe(2-F) |
| 3-fluorophenylalanine | | Phe(3-F) |
| 4-fluorophenylalanine | | Phe(4-F) |
| Penicillamine | | Pen |
| 1,2,3,4-tetrahydro-isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-diamino butyric acid | | Dbu |
| p-aminophenylalanine | | Phe(pNH$_2$) |
| N-methylvaline | | MeVal |
| Homocysteine | | hCys |
| Homoserine | | hSer |
| ε-amino hexanoic acid | | Aha |
| δ-amino valeric acid | | Ava |
| 2,3-diaminobutyric acid | | Dab |

The compounds that are encompassed within the scope of the invention are partially defined in terms of amino acid residues of designated classes. The amino acids may be generally categorized into three main classes: hydrophilic amino acids, hydrophobic amino acids and Cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfanyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classification are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded of which the peptides and peptide analogues of the invention may be composed include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall conveniently into the categories defined above.

The classifications of the above-described genetically encoded and non-encoded amino acids are summarized in Table 1, below. It is to be understood that Table 1 is for illustrative purposes only and does not purport to be an exhaustive list of amino acid residues which may comprise the peptides and peptide analogues described herein. Other amino acid residues which are useful for making the peptides and peptide analogues described herein can be found, e.g., in Fasman, 1989, *CRC Practical Handbook of Biochemistry and Molecular Biology*, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 1

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |

TABLE 1-continued

| Classification | Genetically Encoded | Genetically Non-Encoded |
|---|---|---|
| Hydrophilic | | |
| Acidic | D, E | |
| Basic | H, K, R | Dpr, Orn, hArg, Phe(p-NH$_2$), DBU, A$_2$BU |
| Polar | Q, N, S, T, Y | Cit, AcLys, MSO, hSer |
| Cysteine-Like | C | Pen, hCys, β-methyl Cys |

The designation $Z_n$ in each case represents an amino acid or other moiety capable of forming covalent linkages with other $Z_n$ so as to allow cyclization of the peptide. Examples of amino acid residues which are capable of forming covalent linkages with one another include cysteine-like amino acids such Cys, hCys, β-methyl Cys and Pen, which are capable of forming disulfide bridges with one another. Preferred cysteine-like amino acid residues include Cys and Pen.

Amino acids used to cyclize a peptide need not be cysteine-like amino acids. Pairs of amino acids that have side chain functional groups capable of forming covalent linkages with one another can also be used. Such pairs of functional groups are known to those of skill in the art and include, inter alia, —COOH and —OH, —COOH and —NH$_2$, and —COOH and —SH. Thus, pairs of amino acids that can be used to cyclize a peptide include, inter alia, Asp and Lys; Glu and Lys; Asp and Arg; Glu and Arg; Asp and Ser; Glu and Ser; Asp and Thr; Glu and Thr; Asp and Cys; and Glu and Cys. Other pairs of amino acids which can be used to cyclize the peptide will be apparent to those skilled in the art.

It will also be recognized that $Z_n$ groups used to cyclize a peptide need not be amino acids. Thus, $Z_n$ may be any molecule having three functional groups—one functional group capable of forming a covalent linkage with a terminus of the peptide, a second functional group capable of forming a covalent linkage with the second functional group of another $Z_n$, and a third functional group capable of forming a covalent linkage with hydrophobic moieties $B_n$. Molecules having suitable functional groups will be apparent to those skilled in the art. Examples of functional groups capable of forming a covalent linkage with the amino terminus of a peptide include carboxylic acids and esters. Examples of functional groups capable of forming a covalent linkage with the carboxyl terminus of a peptide include —OH, —SH, —NH$_2$ and —NHR where R is (C$_1$–C$_6$) alkyl, (C$_1$–C$_6$) alkenyl and (C$_1$–C$_6$) alkynyl.

A variety of interlinkages useful to cyclize a peptide can be generated by reaction between two $Z_n$. $Z_n$ with functional groups suitable for forming such interlinkages, as well as reaction conditions suitable for forming such interlinkages, will be apparent to those of skill in the art. Preferably, the reaction conditions used to cyclize the peptides are sufficiently mild so as not to degrade or otherwise damage the peptide. Suitable groups for protecting the various functionalities as necessary are well known in the art (see, e.g., Greene & Wuts, 1991, 2nd ed., John Wiley & Sons, NY), as are various reaction schemes for preparing such protected molecules.

The designation $B_n$ in each case represents a hydrophobic moiety. While not intending to be bound by any particular theory, it is believed that when placed in aqueous solution, these hydrophobic moieties interact so as to confer the peptide with structural stability. A significant hydrophobic interaction for conferring structural stability is thought to be stacking of aromatic rings. Thus, in a preferred embodiment, each $B_n$ designates a peptide of 1–6 amino acids, at least one of which is an aromatic amino acid or an aromatic or heteroaromatic moiety. $B_n$ may be illustrated as $X_{32}$—$X_{33}$—$X_{34}$—$X_{35}$—$X_{36}$—$X_{37}$≡ wherein $X_n$ is an amino acid, at least one of which is an aromatic amino acid. Preferably, $X_{32}$—$X_{33}$—$X_{34}$ are absent and $X_{37}$ is an aromatic amino acid. More preferably, $X_{32}$—$X_{33}$—$X_{34}$—$X_{35}$—$X_{36}$ are absent and $X_{37}$ is an aromatic amino acid. Suitable aromatic amino acids include Tyr, Phe and Trp, with Tyr and Phe being preferred. Suitable aromatic or heteroaromatic moieties include phenyl, naphthyl, purine, pyrimidine, and the like.

In the peptides of formulae (II)–(IV), the symbol "—" between amino acid residues $X_n$ generally designates a backbone interlinkage. Thus, the symbol "—" usually designates an amide linkage (—C(O)—NH). It is to be understood, however, that in all of the peptides described in the specific embodiments herein, one or more amide linkages may optionally be replaced with a linkage other than amide, preferably a substituted amide or an isostere of an amide linkage. Thus, while the various $X_n$ have generally been described in terms of amino acids, one having skill in the art will recognize that in embodiments having non-amide linkages, the term "amino acid" refers to other bifunctional moieties having side-chain groups similar to the side chains of the amino acids. For example, in embodiments having non-amide linkages, the phrase "acidic amino acid" refers to a bifunctional molecule capable of forming the desired backbone interlinkages and which has a side chain group similar to the side chain of an acidic amino acid. Substituted amides generally include groups of the formula —C(O)—NR, where R is (C$_1$–C$_6$) alkyl, (C$_1$–C$_6$) alkenyl, (C$_1$–C$_6$) alkynyl, substituted (C$_1$–C$_6$) alkyl, substituted (C$_1$–C$_6$) alkenyl or substituted (C$_1$–C$_6$) alkynyl. Isosteres of amide generally include, but are not limited to, —CH$_2$NH—, —CH$_2$S—, —CH$_2$CH$_2$, —CH=CH— (cis and trans), —C(O)CH$_2$—, —CH(OH)CH$_2$— and —CH$_2$SO—.

Compounds having such linkages and methods for preparing such compounds are well-known in the art (see, e.g., Spatola, 1983, *Vega Data* 1(3) for a general review); Spatola, 1983, "Peptide Backbone Modifications" In: *Chemistry and Biochemistry of Amino Acids Peptides and Proteins* (Weinstein, ed.), Marcel Dekker, New York, p. 267 (general review); Morley, 1980, *Trends Pharm. Sci.* 1:463–468; Hudson et al., 1979, *Int. J. Prot. Res.* 14:177–185 (—CH$_2$NH—, —CH$_2$CH$_2$—); Spatola et al., 1986, *Life Sci.* 38:1243–1249 (—CH$_2$—S); Hann, 1982, *J. Chem. Soc. Perkin Trans. I.* 1:307–314 (—CH=CH—, cis and trans); Almquist et al., 1980, *J. Med. Chem.* 23:1392–1398 (—COCH$_2$—); Jennings-White et al., *Tetrahedron. Lett.* 23:2533 (—COCH$_2$—); European Patent Application EP 45665 (1982) CA:97:39405 (—CH(OH) CH$_2$—); Holladay et al., 1983, *Tetrahedron Lett.* 24:4401–4404 (—C(OH)CH$_2$—); and Hruby, 1982, *Life Sci.* 31:189–199 (—CH$_2$—S—).

As will be discussed in more detail below, the interlinkage designated by "≡" between residues $B_n$ and/or $Z_n$ and/or $X_n$ in the compounds of formulae (II)–(IV) may also be a linker. Typically, a linker is a bifunctional molecule that spaces one moiety from another. Such linkers, which may be flexible, semi-rigid or rigid, are well-known in the art and include polypeptides such as poly-Gly and poly-Pro, bifunctional hydrocarbons such as aminocaproic acid, δ-aminovaleric acid and β-alanine, carbohydrates, nucleic acids, and the like.

In one specific illustrative embodiment, the compounds of formula (II) are defined as follows:

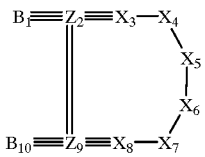 (II)

wherein:

$B_1$ and $B_{10}$ are each independently a peptide of 1–6 amino acids, at least one of which is a hydrophobic amino acid, an aromatic moiety or a heteroaromatic moiety;

$Z_2$ is a moiety that is capable of forming a covalent linkage with $B_1$, $X_3$ and $Z_9$;

$Z_9$ is a moiety that is capable of forming a covalent linkage with $B_{10}$, $X_8$ and $Z_2$;

$X_3$ is absent or a hydrophilic amino acid;

$X_4$ is a hydrophobic amino acid;

$X_5$ is a hydrophilic amino acid;

$X_6$ is a hydrophilic amino acid;

$X_7$ is a hydrophobic or hydrophilic amino acid;

$X_8$ is a hydrophobic or hydrophilic amino acid;

"—" is an amide, substituted amide or an isostere of amide thereof;

"=" is a covalent linkage; and

"≡" is a covalent linkage.

In a preferred embodiment of the invention, the compounds are those of formula (II) wherein:

$B_1$ and $B_{10}$ are each independently a peptide of 1–3 amino acids, at least one of which is an aromatic amino acid;

$Z_2$ and $Z_9$ are each independently a Cys-like amino acid;

$X_3$ is absent or an acidic amino acid;

$X_4$ is an aromatic or apolar amino acid;

$X_5$ is a polar amino acid;

$X_6$ is a polar amino acid;

$X_7$ is an aromatic or polar amino acid;

$X_8$ is an aromatic, apolar or polar amino acid;

"—" is an amide linkage;

"=" is a disulfide linkage; and

"≡" is an amide linkage.

In a particularly preferred embodiment, the compounds of the invention are those of formula (II) wherein:

$B_1$ and $B_{10}$ are each independently Tyr or Phe;

$Z_2$ and $Z_9$ are each Cys;

$X_3$ is absent or Glu;

$X_4$ is Trp or Leu;

$X_5$ is Ser;

$X_6$ is Gln;

$X_7$ is Tyr or Asn;

$X_8$ is Tyr or Leu;

"—" is an amide linkage;

"=" is a disulfide linkage; and

"≡" is an amide linkage.

Particularly preferred peptides of the invention include the following:

| | |
|---|---|
| YCELSQYLCY | (SEQ ID NO:12) |
| YC WSQNLCY | (SEQ ID NO:13) |
| YC WSQNYCY | (SEQ ID NO:14) |
| YC WSQYLCY | (SEQ ID NO:15) |

In a second illustrative embodiment, the compounds of formula (III) are defined as follows:

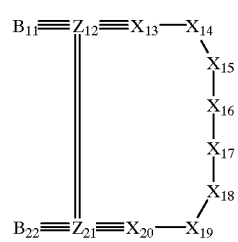 (III)

wherein:

$B_{11}$ and $B_{22}$ are each independently a peptide of 1–6 amino acids, at least one of which is a hydrophobic amino acid, an aromatic moiety or a heteroaromatic moiety;

$Z_{12}$ is a moiety that is capable of forming a covalent linkage with $B_{11}$, $X_{13}$ and $Z_{21}$;

$Z_{21}$ is a moiety that is capable of forming a covalent linkage with $B_{22}$, $X_{20}$ and $Z_{12}$;

$X_{13}$ is absent or hydrophobic amino acid;

$X_{14}$ is absent or a hydrophilic amino acid;

$X_{15}$ is a hydrophilic or hydrophobic amino acid;

$X_{16}$ is a hydrophilic amino acid;

$X_{17}$ is absent or a hydrophobic amino acid;

$X_{18}$ is a hydrophilic amino acid;

$X_{19}$ is a hydrophilic amino acid;

$X_{20}$ is a hydrophilic amino acid;

"—" is an amide, a substituted amide or an isostere of amide thereof;

"=" is a covalent linkage; and

"≡" is a covalent linkage.

In a preferred embodiment, the compounds are those of formula (III) wherein:

$B_{11}$ and $B_{22}$ are each independently a peptide of 1–3 amino acids, at least one of which is an aromatic amino acid;

$Z_{12}$ and $Z_{21}$ are each independently a Cys-like amino acid;

$X_{13}$ is absent or an aromatic amino acid;

$X_{14}$ is absent or a polar amino acid;

$X_{15}$ is a basic, polar or apolar amino acid;

$X_{16}$ is a polar amino acid;

$X_{17}$ is absent or an apolar amino acid $X_{18}$ is an acidic amino acid;

$X_{19}$ is a polar amino acid;

$X_{20}$ is a basic amino acid;

"—" is an amide linkage;

"=" is a disulfide linkage; and

"≡" is an amide linkage.

In a particularly preferred embodiment, the compounds are those of formula (III), wherein:

$B_{11}$ and $B_{22}$ are each independently Tyr or Phe;
$Z_{12}$ and $Z_{21}$ are each Cys;
$X_{13}$ is absent or Phe;
$X_{14}$ is absent or Thr;
$X_{15}$ is Ala, Asn or Arg;
$X_{16}$ is Ser;
$X_{17}$ is absent or Val;
$X_{18}$ is Glu;
$X_{19}$ is Asn;
$X_{20}$ is Arg or His;
"—" is an amide linkage;
"=" is a disulfide linkage; and
"≡" is an amide linkage.

Particularly preferred peptides of the invention include the following:

| | |
|---|---|
| YC FTASENH CY | (SEQ. ID NO:16) |
| YC FTNSENH CY | (SEQ. ID NO:17) |
| YC FTRSENH CY | (SEQ. ID NO:18) |
| FC  ASENH CY | (SEQ. ID NO:19) |
| YC  ASENH CY | (SEQ. ID NO:20) |
| FC  NSENH CY | (SEQ. ID NO:21) |
| FC  NSENR CY | (SEQ. ID NO:22) |
| FC  NSVENR CY | (SEQ. ID NO:23) |

In a third illustrative embodiment, the compounds of formula (IV) are defined as follows:

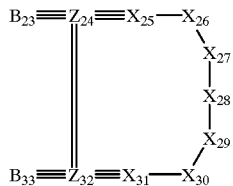

(IV)

wherein:
$B_{23}$ and $B_{33}$ are each independently a a peptide of 1–6 amino acids, at least one of which is a hydrophobic amino acid, an aromatic moiety or a heteroaromatic moiety;
$Z_{24}$ is a moiety that is capable of forming a covalent linkage with $B_{23}$, $X_{25}$ and $Z_{32}$;
$Z_{32}$ is a moiety that is capable of forming a covalent linkage with $B_{33}$, $X_{31}$ and $Z_{24}$;
$X_{25}$ is absent or a hydrophilic amino acid;
$X_{26}$ is a hydrophilic amino acid;
$X_{27}$ is a hydrophilic amino acid;
$X_{28}$ is a hydrophobic amino acid;
$X_{29}$ is a hydrophobic amino acid;
$X_{30}$ is absent or a hydrophilic amino acid;
$X_{31}$ is absent or a hydrophobic amino acid;
"—" is an amide, a substituted amide or an isostere of amide;
"=" is a covalent linkage; and
"≡" is a covalent linkage.

In a preferred embodiment, the compounds are those of formula (IV) wherein:
$B_{23}$ and $B_{33}$ are each independently a peptide of 1–3 amino acids, at least one of which is an aromatic amino acid;
$Z_{24}$ and $Z_{32}$ are each independently a Cys-like amino acid;
$X_{25}$ is absent or a basic amino acid;
$X_{26}$ is a basic amino acid;
$X_{27}$ is an acidic amino acid;
$X_{28}$ is an apolar amino acid;
$X_{29}$ is an apolar amino acid;
$X_{30}$ is absent or a polar amino acid;
$X_{31}$ is absent or an apolar amino acid;
"—" is an amide linkage;
"=" is a disulfide linkage; and
"≡" is an amide linkage.

In a particularly preferred embodiment, the compounds of the invention or analogues thereof are those of formula (IV), wherein:
$B_{23}$ and $B_{33}$ are each independently Tyr or Phe;
$Z_{24}$ and $Z_{32}$ are each Cys;
$X_{25}$ is absent or Arg;
$X_{26}$ is Lys;
$X_{27}$ is Glu;
$X_{28}$ is Leu, Pro or Met;
$X_{29}$ is Gly;
$X_{30}$ is absent or Gln;
$X_{31}$ is absent or Val;
"—" is an amide linkage;
"=" is a disulfide linkage; and
"≡" is an amide linkage.

Particularly preferred peptides of the invention include the following:
YC RKELGQV CY (SEQ. ID NO:24)

| | |
|---|---|
| YC  KEPGQ CY | (SEQ. ID NO:25) |
| YC RKEMG  CY | (SEQ. ID NO:26) |
| FC RKEMG  CY | (SEQ. ID NO:27) |

In all of the aforementioned embodiments of the invention, it is to be understood that the phrase "amino acid" also refers to bifunctional moieties having amino acid-like side chains, as previously described.

Generally, active peptides or peptide analogues of the invention are those that exhibit at least about 15% inhibition of TNF-R:TNF interactions as measured in vitro assays such as those described in Section 6, infra. Preferably, active peptides of the invention or analogues thereof will exhibit at least about 20% to 50% or even 80% or ore inhibition of TNF-R:TNF-α binding interactions.

5.3. Preparation of Peptides and Peptide Analogues 5.3.1. Chemical Synthesis

The peptides of the invention or analogues thereof, may be prepared using virtually any art-known technique for the preparation of peptides and peptide analogues. For example, the peptides may be prepared in linear or non-cyclized form using conventional solution or solid phase peptide syntheses and cyclized using standard chemistries. Preferably, the chemistry used to cyclize the peptide will be sufficiently mild so as to avoid substantially degrading the peptide. Suitable procedures for synthesizing the peptides described herein as well as suitable chemistries for cyclizing the peptides are well known in the art.

Formation of disulfide linkages, if desired, is generally conducted in the presence of mild oxidizing agents.

Chemical, enzymatic or photolytic oxidation agents may be used. Various methods are known in the art, including those described, for example, by Tam, J. P. et al., 1979, *Synthesis* 955–957; Stewart et al., 1984, *Solid Phase Peptide Synthesis*, 2d Ed., Pierce Chemical Company Rockford, Ill.; Ahmed et al., 1975, *J. Biol. Chem.* 250:8477–8482; and Pennington et al., 1991 *Peptides* 1990 164–166, Giralt and Andreu, Eds., ESCOM Leiden, The Netherlands. An additional alternative is described by Kamber et al., 1980, *Helv Chim Acta* 63:899–915. A method conducted on solid supports is described by Albericio, 1985, *Int. J. Peptide Protein Res.* 26:92–97. Any of these methods may be used to form disulfide linkages in the peptides of the invention. Preferred methods for effecting disulfide-bridge formation for the peptides described herein are provided in the examples.

5.3.2. Recombinant Synthesis

If the peptide is composed entirely of gene-encoded amino acids, or a portion of it is so composed, the peptide or the relevant portion may also be synthesized using conventional recombinant genetic engineering techniques. The isolated peptides, or segments thereof, are then condensed, and oxidized, as previously described, to yield a cyclic peptide.

For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the linear form of the cyclic peptide. Depending on the expression system used, the expressed peptide is then isolated by procedures well-established in the art. Methods for recombinant protein and peptide production are well known in the art (see, e.g., Maniatis et al., 1989, *Molecular Cloning A Laboratory Manual*, Cold Spring Harbor Laboratory, N.Y.; and Ausubel et al., 1989, *Current Protocols in Molecular Biology*, Greene Publishing Associates and Wiley Interscience, N.Y.).

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J.* 6:307–311) may be used; alternatively, plant promoters such as the small subunit of RUBISCO (Coruzzi et al., 1984, *EMBO J.* 3:1671–1680; Broglie et al., 1984, *Science* 224:838–843) or heat shock promoters, e.g., soybean hsp17.5-E or hsp17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, *Methods for Plant Molecular Biology*, Academic Press, NY, Section VIII, pp. 421–463; and Grierson & Corey, 1988, *Plant Molecular Biology*, 2d Ed., Blackie, London, Ch. 7–9.

In one insect expression system that may be used to produce the peptides of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, *J. Virol.* 46:584; Smith, U.S. Pat. No. 4,215,051). Further examples of this expression system may be found in *Current Protocols in Molecular Biology*, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, *Proc. Natl. Acad. Sci.* (*USA*) 81:3655–3659). Alternatively, the vaccinia 7.5 K promoter may be used, (see, e.g., Mackett et al., 1982, *Proc. Natl. Acad. Sci.* (*USA*) 79:7415–7419; Mackett et al., 1984, *J. Virol.* 49:857–864; Panicali et al., 1982, *Proc. Natl. Acad. Sci.* 79:4927–4931).

Other expression systems for producing linear or non-cyclized forms of the cyclic peptides of the invention will be apparent to those having skill in the art.

5.3.3. Purification of the Peptides and Peptide Analogues

The peptides and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art.

For affinity chromatography purification, any antibody which specifically binds the peptides or peptide analogues may be used. For the production of antibodies, various host animals, including but not limited to rabbits, mice, rats, etc., may be immunized by injection with a linear or cyclic peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Koehler and Milstein, 1975, *Nature* 256:495–497, the human B-cell hybridoma technique, Kosbor et al., 1983, *Immunology Today* 4:72; Cote et al., 1983, *Proc. Natl. Acad. Sci. U.S.A.* 80:2026–2030 and the EBV-hybridoma technique (Cole et al., 1985, *Monoclonal Antibodies and Cancer Therapy*, Alan R. Liss, Inc., pp. 77–96 (1985)). In addition, techniques developed for the production of "chimeric antibodies" (Morrison et al., 1984, *Proc. Natl. Acad. Sci. U.S.A.* 81:6851–6855; Neuberger et al., 1984, *Nature* 312:604–608; Takeda et al., 1985, *Nature* 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce cyclic peptide-specific single chain antibodies.

Antibody fragments which contain deletions of specific binding sites may be generated by known techniques. For example, such fragments include but are not limited to F(ab')$_2$ fragments, which can be produced by pepsin digestion of the antibody molecule and Fab fragments, which can be generated by reducing the disulfide bridges of the F(ab')$_2$ fragments. Alternatively, Fab expression libraries may be constructed (Huse et al., 1989, *Science* 246:1275–1281) to allow rapid and easy identification of monoclonal Fab fragments with the desired specificity for the cyclic peptide of interest.

The antibody or antibody fragment specific for the desired cyclic peptide can be attached, for example, to agarose, and the antibody-agarose complex is used in immunochromatography to purify cyclic peptides of the invention. See, Scopes, 1984, *Protein Purification: Principles and Practice*, Springer-Verlag New York, Inc., NY, Livingstone, 1974, *Methods Enzymology: Immunoaffinity Chromatography of Proteins* 34:723–731.

5.4. Uses of Peptides and Peptide Analogues Designed from a TNF-R Superfamily Member The compounds of the present invention are useful for inhibiting the biological activities of ligands for members of the TNF-R superfamily. Ligands for all TNF-R superfamily members have been identified and isolated, and they are also classified into a superfamily based on their structural similarities. All members of this ligand family are capable of regulating diverse cellular responses, including proliferation, activation, differentiation, and even cell death by apoptosis or cytotoxicity. Since all TNF-R superfamily members are expressed on lymphocytes, particularly T cells, their corresponding ligands are able to regulate immune responses. A second commonly shared feature of all TNF ligand superfamily members is their ability to induce cell death.

As an illustration, CD40 is expressed on B cells and cross-linking of this receptor by its ligand induces B cell activation, including IgE secretion. Therefore, inhibition of CD40 interactions with its ligand down-regulates B cell responses, and may be used to treat autoimmunity and hypersensitivity. In contrast, the Fas ligand cross-links Fas antigen (CD95) expressed on activated T cells and B cells, and induces cell death. The inhibition of Fas ligand and Fas antigen interactions has been used to prevent transplantation rejections. Fas ligand has been proposed as a potential immunosuppressive agent, based on the observation that the expression of the Fas ligand by Sertoli cells accounted for the immune-privileged nature of testis by inducing apoptosis of Fas-expressing T cells (Bellgrau et al., 1995, *Nature* 377:360). Therefore, compounds of the invention which inhibit the binding of Fas with its ligand may be used to augment immune responses in certain settings.

In a preferred embodiment of the invention, a compound of the invention inhibits TNF binding to its receptors. Since TNF-α and TNF-β bind to the same receptors, such compounds are expected to inhibit both TNF-α and TNF-β activities. Such compounds may be used for the treatment of pathological conditions in which the biological activities of TNF play an active role. Such conditions, include, but are not limited to, acute and chronic inflammation, cachexia, septic shock, graft-versus-host disease, transplantation rejection, hypersensitivity, immune complex disease, malaria, and autoimmunity such as multiple sclerosis, rheumatoid arthritis, peridontal disease and non-insulin-dependent diabetes.

5.4.1. Formulation and Route of Administration

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

5.4.2. Effective Dosage

The compounds of the invention will generally be used in an amount effective to achieve the intended purpose. For use to treat or prevent TNF-associated disorders, the compounds of the invention, or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that inhibits 50% of TNF-R:TNF-binding interactions). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of TNF-associated disorders, the drugs that may be used in combination with the compounds of the invention include, but are not limited to, steroid and non-steroid anti-inflammatory agents.

5.4.3. Toxicity

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics,* Ch.1, p.1).

The invention having been described, the following examples are offered by way of illustration and not limitation.

6. EXAMPLE

Exocyclic Peptides Derived from TNF-R Antagonize TNF-α Activities

6.1. Materials and Methods

6.1.1. Reagents

Human recombinant TNF-α and the 125I-labeled TNF-α were obtained from Amersham Life Science, Inc. (Arlington Heights, Ill.). TNF-R(I) or p55 extracellular domain-IgG heavy chain chimeric protein was prepared by expression of a cDNA construct (Peppel et al., 1991, *J. Exp. Med.* 174:1483; Williams et al., 1995, *Immunol.* 84:433). Anti-TNF-α monoclonal antibody was made according to Doring et al. (1994, *Molecular Immunol.* 31:1059) and anti-TNF-R(I) monoclonal antibody (htr-9) was obtained from BMA Biomedicals AG (Augst, Switzerland).

6.1.2. Molecular Modeling

Computer modeling was performed using Quanta 4.0 (Molecular Simulation Inc., Mass.). The model peptides were constructed from their sequences and folded using CHARMM. The side chains of amino acid residues were first positioned to permitted conformation using Ponders rotamer (Ponder et al., 1987, *J. Mol. Biol.* 193:775–791) database provided in QUANTA. Then the folded peptides were minimized to convergence with dielectric constant set to 80.

The crystal structure of the TNF-β/TNF-R(I) complex (Banner et al., 1993, *Cell* 73:431) was utilized to determine the binding sites of TNF-R for TNF-α. The first (56–73) and second (76–83) loops of domain 2 and the first loop (107–114) of domain 3 of the TNF-R were explored for use in designing peptides. The essential amino acid sequences of TNF-R for binding interactions with TNF-α were identified as structural templates by superimposing TNF-α to TNFβ complexed with its cognate receptor. Then, 5–8 amino acid-long peptides derived from TNF-R as shown in Table 2 were used as templates for the design of exocyclic peptides.

Additional peptides were derived from CDR sequences of a light chain of an anti-TNF-α neutralizing antibody, CDR1L of Di62 (Doring et al., 1994, *Mol. Immunol.* 31:1059). Exocyclic modifications such as peptide cyclization and addition of aromatic amino acids such as Phe and Tyr to the ends of each peptide were performed as described (Zhang et al., 1996, *Nature Biotech.* 14:472; Zhang et al., 1997, *Nature Biotech.* 15:150).

6.1.3. Peptide Synthesis, Cyclization and Purification

Linear peptides were synthesized by solid-phase methods, deprotected, and released from the resin utilizing standard methodology. Peptides were precipitated and purified by high performance liquid chromatography (HPLC) utilizing a C18 column and then lyophilized. The purity of such peptides was greater than 95% as measured by HPLC analysis.

The peptides containing internal Cys residues were oxidized by dissolving them at 100 µg/ml in distilled water adjusted or buffered to pH 8.0–8.5, for example, by $(NH_4)_2CO_3$ with stirring and exposure to air at 4° C. for <10 days until 95% formation of intramolecular disulfide bonds had been confirmed by DTNB (Sigma, St. Louis, Mo.) which determined free sulfhydryls in peptides (Habeeb, 1973, *Anal. Bioch.* 56:60; Angeletti et al., 1996, In Techniques in Protein Chemistry VII, Ed. Marsak, Academic Press, San Diego, Calif., pp. 81–91). Briefly, peptides (100 µg/ml, 50 µl) and DTNB (10 mM, 50 µl) were added to 0.1 M sodium phosphate buffer (pH 8.0, 1 ml), incubated in the dark for 30 minutes, and the absorbance at 420 nm was determined and compared with the linear unoxidized peptides.

The cyclized peptides were lyophilized, purified by HPLC utilizing a C18 preparative column and a size exclusion column Protein-Pak 60 (Waters, Milford, Mass.). The purity of the peptides was shown to be greater than 95% by HPLC analysis. The concentration of each cyclized peptide was calculated based on UV intensity versus the corresponding linear peptide by HPLC analysis.

6.1.4. Competitive Radioreceptor Assay

TNF-R-IgG chimeric protein (100 ng/ml) diluted in 100 µl phosphate buffered saline (PBS) was immobilized onto MicroTest III flexible assay plates (Becton Dickinson, San Jose, Calif.) by incubation at 4° C. overnight. After blocking with PBS containing 1% bovine serum albumin (BSA) for 2 hr. at room temperature and subsequent washing with PBS containing 0.1% Tween 20 (PBS-Tw), $^{125}$I-labeled-TNF-α(1 ng) was preincubated with a peptide solution (100 µl) in PBS for 1 hr. at 37° C. and was added to the TNF-R-coated wells. After 2 hr. incubation at 37° C., the plate was washed with PBS-Tw, and bound radioactivity was measured in Cobra gamma counter (Packard Instruments, Meriden, Conn.).

6.1.5. Flow Cytometry

A human leukemia cell line, U937, was maintained in RPMI-1640 medium supplemented with 10% FCS. In order to quantitate the binding of TNF-α to its cognate receptor expressed on U937 cells, $1 \times 10^5$ cells were re-suspended in PBS containing 0.5% BSA and 0.05% $NaN_3$ (binding buffer). TNF-α (2.5ng) was preincubated with a peptide solution (50 µl) in PBS for 1 hr. at 37° C. and was added to the cells for 1 hr. at 4° C. at a final TNF-α concentration of 50 ng/ml. Then, 50 µl of an anti-TNF receptor antibody at 3 µg/ml in binding buffer were added to the cells for 1 hr. at 4° C. The cells were washed in binding buffer and stained with 50 µl (10 µg/ml) of fluorescein-conjugated goat ant-mouse IgG secondary antibody (GIBCO BRL, Gaithersburg, Md.) for 30 min. at 4° C. in the dark. Following washing in binding buffer, the cells were analyzed using FACScan flow cytometer (Becton Dickinson). The gates were set on the live cell population, and the degree of inhibition of TNF-α/cell binding by peptides was calculated on the basis of mean values of each histogram.

6.1.6. Cytotoxicity Assay

A murine fibroblast cell line, L929, was maintained in Dulbecco's modified Eagle's medium supplemented with 10% FCS, and the medium was replaced with serum free AIM-V medium (GIBCO BRL) immediately before the cells were used for the cytotoxicity assay. L929 cells were seeded at a density of $2 \times 10^5$ cells/ml in 96-well microtiter plates, and incubated for hr. at 37° C. under 5% $CO_2$ in air. TNF-α (7 pg) was preincubated with a peptide solution (80 μl) in PBS for 1 hr. at 37° C. and was added to the cells which had been incubated with actinomycin D (ACT-D) at 1 μg/ml for 2 hr. The cells were incubated with TNF-α adjusted to a final concentration of 50 pg/ml for 7 hr. at 37° C. under 5% $CO_2$, and stained with MTT (3-[4,5-dimethylthiazol-2-yl]2,5-diphenyl-tetrazolium bromide) (Sigma)(Hansen et al., 1989, *J. Immunol. Methods* 119:203). Briefly, 10 μl of a 10 mg/ml solution of MTT were added to each well for 2 hr. at 37° C., and the color of the formazan product was developed by an overnight incubation at 37° C. with 100 μl of extraction buffer (20% SDS in 50% DMF, pH 4.7). The optical density of colored formazan was measured at 600 nm.

6.1.7. Phosphorylation of IRS-1 in Adipocytes

3T3-L1 cells were grown and differentiated into adipocytes as described previously (Garcia de Herreros et al., 1989, *J. Biol. Chem.* 264:19994). After maximal differentiation, (at least 90% of cells differentiated) the cells were starved in 0.2% BSA for 1 day and then treated with TNF-α at a concentration of 50 ng/ml in Leibovitz's L-15 medium/PBS (2 ml/ 2 ml) for 4 hr. at 37 C. without $CO_2$. In certain samples, peptides were preincubated with TNF-α in PBS for 1 hr. at 37° C. before the mixture was added to the starved adipocytes. The cells were then stimulated for 3 min. with insulin (100 nM), washed in ice-cold PBS, and then solubilized in lysis buffer (50 mM Hepes, pH 7.4, 150 mM NaCl, 10 mM EDTA, 10 mM $Na_4P_2O_7$, 1 mM $Na_3VO_4$, 100 mM NaF, 1% Triton X-100 (v/v), 10 g/ml aprotinin, 1 g/ml leupeptin, and 1 mM phenylmethylsulfonyl fluoride). IRS-1 was immunoprecipitated from the cell extracts (1 ml) with an anti-IRS-1 antiserum (5 μl, overnight at 4° C.) and protein A-Sepharose (Sigma) at 20 Al bed volume for 1 hr. at 4° C. After three washes in 50 mM Hepes buffer (pH 7.4) including 1% Triton X-100 (v/v), 0.1% SDS and 150 mM NaCl, the immunoprecipitated proteins were boiled in Laemmli sample buffer for 3 min., and separated on 6% SDS-PAGE. Proteins were then transferred to a nitrocellulose membrane, and Western blot analysis was performed using the ECL Western blot kit (Amersham) according to the manufacturer's instructions. The membrane was first probed with an anti-phosphorylated Tyr antibody (1:20,000) coupled with a secondary labeled antibody, then stripped and reprobed with an anti-IRS-1 antiserum (1:1,000). The intensity of each band was analyzed by Image Quanta densitometer (Molecular Dynamics, Sunnyvale, Calif.), and the reduction of TNF-α-induced insulin resistance by peptides was calculated after subtracting background intensity from each band.

6.2. Results

Amino acid sequences corresponding to three TNF-α-binding loops of TNF-R were used as templates for the synthesis of a number of peptides. Cys residues were included in the linear peptides to enable their cyclization. Their identity was verified by mass spectrometry.

Various exocyclic peptides listed in Table 2 were tested for their ability to inhibit radiolabeled TNF-α binding to TNF-R-chimeric protein. FIG. 2 shows that while peptides designed from three separate loop regions of TNF-R inhibited TNF-α binding to TNF-R, peptides designed from loop 1 of domain 3 (WP9 series) of TNF-R exhibited stronger inhibitory effects than did the peptides designed from loop 1 of domain 2 (WP5 series) and loop 2 of domain 2 (WP8 series) at a concentration of 25 μM. The WP5 series of peptides were developed by comparing the structures of TNF-R loops and CDR1 of an anti-TNF-α antibody. Modifications of the WP5 peptides from Ala to Asn increased their inhibitory activities, but similar modifications of the WP8 peptides did not result in such effects.

Loop 1 of domain 3 of TNF-R was used as a template to design a peptide which contained Gln instead of a charged residue, Glu (WP9Q). When the WP9Q peptide was tested in the competitive radioreceptor assay, it showed a 2-fold higher activity than the best WP5 peptides. Further modified WP9 peptides were compared in a dose-response study, and the WP9QY peptide was shown to exhibit the strongest inhibitory activities, with an $IC_{50}$ at 5 μM (FIG. 3). The WP9QY peptide was modified from WP9Q by replacing Asn in WP9Q with Tyr which enhanced receptor interactions with TNF-α via Trp and Gln which are critical residues for its binding to the receptor. A more compact shape of WP9QY than the other WP peptides also appeared to increase WP9QY interactions with TNF-α as suggested by its slower elution from a size exclusion column on HPLC (FIG. 4).

TABLE 2

Amino Acid Sequences of TNF-α Binding Sites in TNF-R and Exocyclic Peptides Derived from These Sites

| TNF-α Binding Sites in the Receptor | Exocyclic Peptides* | | |
| --- | --- | --- | --- |
| Binding site - 5 | | | |
| TNF-α | WP5 | YC | FTASENH CY |
| 53E 82R 85VSY87 125Q 127E | WP5N | YC | FTNSENH CY |
| | WP5R | YC | FTRSENH CY |
| Receptor (loop 1 of domain2) | WP5J | FC | ASENH CY |
| 60 FTASENH 66 | WP5JY | YC | ASENH CY |
| | WP5JN | FC | NSENH CY |
| | WP5JR | FC | NSENR CY |
| | WP5VR | FC | NSVENR CY |
| | WP1** | YC | SQSVSND CF |
| | WP1R** | FC | VSNDR CY |
| Binding site - 8 | | | |
| TNF-α | | | |
| 65K 67Q 113P 115Y 143L 145A | | | |
| | WP8L | YC | RKELGQV CY |
| Receptor (loop 2 of domain 2) | WP8JP | YC | KEPGQ CY |
| 76 CRKEMGQV 83 | WP8J | YC | RKEMG CY |
| | WP8JF | FC | RKEMG CY |
| Binding site - 9 | | | |
| TNF-α | | | |
| 72THVL75 77T 971 137 N | | | |
| | WP9Q | YC | WSQNL CY |
| Receptor (loop 1 of domain3) | WP9ELY | YC | ELSQYL CY |
| 107 WSENL 111 | WP9Y | YC | WSQNY CY |
| | WP9QY | YC | WSQYL CY |

*Peptides were cyclized with cysteine disulfide bridges
**WP1 and WP1R were derived from an anti-TNF-α antibody (Di62, CDR1L), and the template sequence is QSVSNDV.

U937 cells which express high levels of TNF-R p55 were incubated with TNF-α with or without peptides. The binding of TNF-α to the cells was quantitated by an anti-TNF-R antibody followed by FACS analysis. FIG. 5 demonstrates that while significant binding of anti-receptor antibody to U937 cells was observed, there was a 70% reduction of this binding by pretreatment of the cells with TNF-α. The addition of the WP9QY peptide caused anti-receptor staining to return to a level similar to that with anti-receptor antibody alone. When a similar experiment was performed in a dose-response assay, the WP9QY peptide again exhibited the strongest inhibitory activity as compared to WP9Q and WP5JY peptides (FIG. 6). The WP9QY peptide inhibited TNF-α binding to its cellular receptor with an $IC_{50}$ at 75 μM. Additionally, the peptides were tested for their ability to inhibit the biological effects induced by TNF-α on TNF-sensitive L929 cells (Hennet et al., 1993, *Biochem. J.* 289:587–592). TNF-α induced apoptosis/cytotoxicity of L929 cells, and the WP9QY peptide protected nearly 90% of the cells against such effects of TNF-α at a concentration of 75 μM (FIG. 7). WP9Q also showed dose-dependent inhibitory activity which corresponded to about half of the effects of WP9QY.

Previous studies have shown that 3T3-L1 fibroblastic cell line undergoes differentiation to adipocytes under appropriate culture conditions, and the differentiated cells develop an increased sensitivity to insulin (Garcia de Herreros et al., 1989, *J. Biol. Chem.* 264:19994). Response to insulin stimulation in these cells can be conveniently measured by tyrosine phosphorylation of insulin receptor substrate-1 (IRS-1). The addition of TNF-α has been shown to diminish insulin-induced phosphorylation of this substrate, suggesting that TNF-α may play a role in obesity-induced insulin resistance (Kanety et al., 1995, *J. Biol. Chem.* 270:23780).

The WP9QY peptide was tested for its ability to inhibit TNF-α-induced-insulin resistance. 3T3-L1 cells were induced to differentiate into adipocytes, stimulated with insulin and Tyr phosphorylation of IRS-1 was assayed by immunoprecipitating the cell extracts with anti-IRS-1 antiserum followed by Western blot analysis with an anti-phosphorylated Tyr antibody. FIG. 8A shows that phosphorylated IRS-1 was detected in cells stimulated with 100 nM insulin. In contrast, when TNF-α (50 ng/ml) was added to the cells prior to insulin, the same IRS-1 band was not detectable, confirming that TNF-α inhibited insulin stimulation of Tyr phosphorylation of IRS-1. However, when the WP9QY peptide was preincubated with TNF-α, it antagonized the effects of TNF-α in a dose-dependent manner, as evidenced by the reappearance of the phosphorylated IRS-1 band as the concentrations of the peptide increased. FIG. 8B demonstrates that IRS-1 was present in all tested samples.

In conclusion, peptides derived from certain loop structures of TNF-R inhibit the binding of TNF-α to cell surface TNF-R, indicating that these loops correspond to binding sites of TNF-R to its ligands. The peptides also antagonize the biological effects of TNF-α in preventing the induction of apoptosis/cytotoxicity and insulin resistance in target cells. Importantly, the most effective peptide is derived from loop 1 of domain 3 of TNF-R, which may represent a critical binding site between TNF-R and TNF-α interactions. FIG. 9 presents a three-dimensional model of TNF-α (right side) and TNF-R (left side) interactions. The darkened portion of the loop structure in TNF-R represents the location of loop 1 of domain 3.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A compound having the formula:

$$B_1 = Z_2 = X_3 - X_4 \diagdown X_5 \mid X_6 \diagup$$
$$B_{10} = Z_9 = X_8 - X_7$$
(II)

wherein:

$B_1$ and $B_{10}$ are each independently a peptide of 1–6 amino acids, at least one of which is a hydrophobic amino acid, an aromatic moiety, or a heteroaromatic moiety;

$Z_2$ is a moiety that is capable of forming a covalent linkage with $B_1$, $X_3$, and $Z_9$;

$Z_9$ is a moiety that is capable of forming a covalent linkage with $B_{10}$, $X_8$, and $Z_2$;

$X_3$ is absent or a hydrophilic amino acid;

$X_4$ is a hydrophobic amino acid;

$X_5$ is a hydrophilic amino acid;

$X_6$ is a hydrophilic amino acid;

$X_7$ is a hydrophobic or hydrophilic amino acid;

$X_8$ is a hydrophobic amino acid;

"—" is an amide, substituted amide, or an isostere of amide thereof;

"=" is a covalent linkage; and

"≡" is a covalent linkage.

2. A pharmaceutical composition, comprising the compound of claim 1 and a pharmaceutical excipient carrier or an excipient.

3. A method of selecting an agent which antagonizes TNF activities, comprising incubating TNF with the compound of claim 1 in the presence of a test agent, and measuring a decrease in TNF binding to the compound.

4. A compound having the formula:

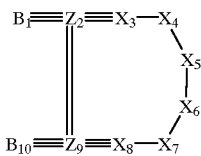

(II)

wherein:
- $B_1$ and $B_{10}$ are each independently a peptide of 1–3 amino acids, at least one of which is an aromatic acid;
- $Z_2$ and $Z_9$ are each independently a Cys-like amino acid;
- $X_3$ is absent or an acidic amino acid;
- $X_4$ is an aromatic or apolar amino acid;
- $X_5$ is a polar amino acid;
- $X_6$ is a polar amino acid;
- $X_7$ is an aromatic or polar amino acid;
- $X_8$ is an aromatic, apolar, or polar amino acid;
- "—" is an amide linkage;
- "=" is a disulfide linkage; and
- "≡" is an amide linkage.

5. The compound of claim 4, wherein:
- $B_1$ and $B_{10}$ are each independently Tyr or Phe;
- $Z_2$ and $Z_9$ are each Cys;
- $X_3$ is absent or Glu;
- $X_4$ is Trp or Leu;
- $X_5$ is Ser;
- $X_6$ is Gln;
- $X_7$ is Tyr or Asn;
- $X_8$ is Tyr or Leu;
- "—" is an amide linkage;
- "=" is a disulfide linkage; and
- "≡" is an amide linkage.

6. The compound of claim 5, wherein said compound is selected from the group consisting of WP9Q (SEQ ID NO:13), WP9ELY (SEQ ID NO:12), WP9Y (SEQ ID NO:14) and WP9QY (SEQ ID NO:15).

7. A pharmaceutical composition, comprising the compound of claim 4 and a pharmaceutical excipient carrier or an excipient.

8. A method of selecting an agent which antagonizes TNF activities, comprising incubating TNF with the compound of claim 4 in the presence of a test agent, and measuring a decrease in TNF binding to the compound.

9. A compound having the formula:

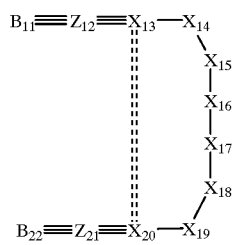

(III)

wherein:
- $B_{11}$ and $B_{22}$ are each independently a peptide of 1–6 amino acids, at least one of which is a hydrophobic amino acid, an aromatic moiety or a heteroaromatic moiety;
- $Z_{12}$ is a moiety that is capable of forming a covalent linkage with $B_{11}$, $X_{13}$ and $Z_{21}$;
- $Z_{21}$ is a moiety that is capable of forming a covalent linkage with $B_{22}$, $X_{20}$ and $Z_{12}$;
- $X_{13}$ is absent or hydrophobic amino acid;
- $X_{14}$ is absent or a hydrophilic amino acid;
- $X_{15}$ is a hydrophilic or hydrophobic amino acid;
- $X_{16}$ is a hydrophilic amino acid;
- $X_{17}$ is absent or a hydrophobic amino acid;
- $X_{18}$ is a hydrophilic amino acid;
- $X_{19}$ is a hydrophilic amino acid;
- $X_{20}$ is a hydrophilic amino acid;
- "—" is an amide, a substituted amide or an isostere of amide thereof;
- "=" is a covalent linkage; and
- "≡" is a covalent linkage.

10. The compound of claim 9, wherein:
- $B_{11}$ and $B_{22}$ are each independently a peptide of 1–3 amino acids, at least one of which is an aromatic amino acid;
- $Z_{12}$ and $Z_{21}$ are each independently a Cys-like amino acid;
- $X_{13}$ is absent or an aromatic amino acid;
- $X_{14}$ is absent or a polar amino acid;
- $X_{15}$ is a basic, polar or apolar amino acid;
- $X_{16}$ is a polar amino acid;
- $X_{17}$ is absent or an apolar amino acid
- $X_{18}$ is an acidic amino acid;
- $X_{19}$ is a polar amino acid;
- $X_{20}$ is a basic amino acid;
- "—" is an amide linkage;
- "=" is a disulfide linkage; and
- "≡" is an amide linkage.

11. The compound of claim 10, wherein:
- $B_{11}$ and $B_{22}$ are each independently Tyr or Phe;
- $Z_{12}$ and $Z_{21}$ are each Cys;
- $X_{13}$ is absent or Phe;
- $X_{14}$ is absent or Thr;
- $X_{15}$ is Ala, Asn or Arg;
- $X_{16}$ is Ser;
- $X_{17}$ is absent or Val;
- $X_{18}$ is Glu;
- $X_{19}$ is Asn;
- $X_{20}$ is Arg or His;
- "—" is an amide linkage;
- "=" is a disulfide linkage; and
- "≡" is an amide linkage.

12. The compound of claim 11, wherein said compound is selected from the group consisting of WP5 (SEQ ID NO:16), WP5N (SEQ ID NO:17), WP5R (SEQ ID NO:18), WP5J (SEQ ID NO:19), WP5JY (SEQ ID NO:20), WP5JN (SEQ ID NO:21), WP5JR (SEQ ID NO:22) and WP5VR (SEQ ID NO:23).

13. A pharmaceutical composition, comprising the compound of claim 9 and a pharmaceutical excipient carrier or an excipient.

14. A method of selecting an agent which antagonizes TNF activities, comprising incubating TNF with the compound of claim 9 in the presence of a test agent, and measuring a decrease in TNF binding to the compound.

15. A compound having the formula:

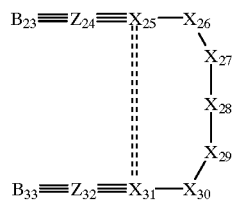

(IV)

wherein:

$B_{23}$ and $B_{33}$ are each independently a peptide of 1–6 amino acids, at least one of which is a hydrophobic amino acid, an aromatic moiety or a heteroaromatic moiety;

$Z_{24}$ is a moiety that is capable of forming a covalent linkage with $B_{23}$, $X_{25}$ and $Z_{32}$;

$Z_{32}$ is a moiety that is capable of forming a covalent linkage with $B_{33}$, $X_{31}$ and $Z_{24}$;

$X_{25}$ is absent or a hydrophilic amino acid;

$X_{26}$ is a hydrophilic amino acid;

$X_{27}$ is a hydrophilic amino acid;

$X_{28}$ is a hydrophobic amino acid;

$X_{29}$ is a hydrophobic amino acid;

$X_{30}$ is absent or a hydrophilic amino acid;

$X_{31}$ is absent or a hydrophobic amino acid;

"—" is an amide, a substituted amide or an isostere of amide;

"=" is a covalent linkage; and

"≡" is a covalent linkage.

16. The compound of claim 15, wherein:

$B_{23}$ and $B_{33}$ are each independently a peptide of 1–3 amino acids, at least one of which is an aromatic amino acid;

$Z_{24}$ and $Z_{32}$ are each independently a Cys-like amino acid;

$X_{25}$ is absent or a basic amino acid;

$X_{26}$ is a basic amino acid;

$X_{27}$ is an acidic amino acid;

$X_{28}$ is an apolar amino acid;

$X_{29}$ is an apolar amino acid;

$X_{30}$ is absent or a polar amino acid;

$X_{31}$ is absent or an apolar amino acid;

"—" is an amide linkage;

"=" is a disulfide linkage; and

"≡" is an amide linkage.

17. The compound of claim 16, wherein:

$B_{23}$ and $B_{33}$ are each independently Tyr or Phe;

$Z_{24}$ and $Z_{32}$ are each Cys;

$X_{25}$ is absent or Arg;

$X_{26}$ is Lys;

$X_{27}$ is Glu;

$X_{28}$ is Leu, Pro or Met;

$X_{29}$ is Gly;

$X_{30}$ is absent or Gln;

$X_{31}$ is absent or Val;

"—" is an amide linkage;

"=" is a disulfide linkage; and

"≡" is an amide linkage.

18. The compound of claim 17, wherein said compound is selected from the group consisting of WP8L (SEQ ID NO:24), WP8JP (SEQ ID NO:25), WP8J (SEQ ID NO:26) and WP8JF (SEQ ID NO:27).

19. A pharmaceutical composition, comprising the compound of claim 15 and a pharmaceutical excipient carrier or an excipient.

20. A method of selecting an agent which antagonizes TNF activities, comprising incubating TNF with the compound of claim 15 in the presence of a test agent, and measuring a decrease in TNF binding to the compound.

21. A method of selecting an agent which antagonizes TNF activities, comprising incubating TNF in the presence of a test agent with a compound of the formula

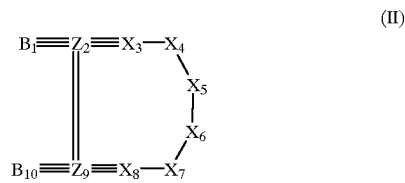

(II)

wherein:

$B_1$ and $B_{10}$ are each independently a peptide of 1–6 amino acids, at least one of which is a hydrophobic amino acid, an aromatic moiety, or a heteroaromatic moiety;

$Z_2$ is a moiety that is capable of forming a covalent linkage with $B_1$, $X_3$, and $Z_9$;

$Z_9$ is a moiety that is capable of forming a covalent linkage with $B_{10}$, $X_8$, and $Z_2$;

$X_3$ is absent or a hydrophilic amino acid:

$X_4$ is a hydrophobic amino acid;

$X_5$ is a hydrophilic amino acid;

$X_6$ is a hydrophilic amino acid;

$X_7$ is a hydrophobic or hydrophilic amino acid;

$X_8$ is a hydrophobic or hydrophilic amino acid;

"—" is an amide, substituted amide, or an isostere of amide thereof;

"=" is a covalent linkage; and

"≡" is a covalent linkage; and measuring a decrease in TNF binding to the compound.

* * * * *

UNITED STATES PATENT AND TRADEMARK OFFICE
CERTIFICATE OF CORRECTION

PATENT NO. : 6,265,535 B1
DATED : July 24, 2001
INVENTOR(S) : Greene et al.

It is certified that error appears in the above-identified patent and that said Letters Patent is hereby corrected as shown below:

Column 14,
Line 28, please delete "Z12" and insert therefor -- $Z_{12}$ --;

Column 16,
Line 51, please delete "ore" and insert therefor -- move --;

Column 23,
Line 37, please delete "1251" and insert therefor -- $125_I$ --;

Column 25,
Line 42, please delete "20A1" and insert therefor -- $20\mu l$ --;

Column 27,
Line 7, please insert a new paragraph after "$\mu M.$" and before "Additionally";

Signed and Sealed this

Eleventh Day of June, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO. : 6,265,535 B1
APPLICATION NO. : 08/866545
DATED : July 24, 2001
INVENTOR(S) : Mark I. Greene et al.

It is certified that error appears in the above-identified patent and that said Letters Patent is hereby corrected as shown below:

Column 43, lines 52-60, formula (III) in claim 9 should appear as follows:

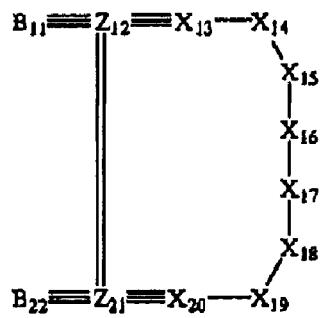

Column 45, lines 4-10, formula (IV) in claim 15 should appear as follows:

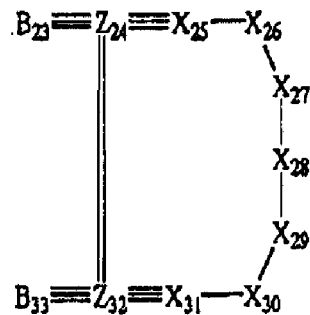

Signed and Sealed this

Fifth Day of February, 2008

JON W. DUDAS
*Director of the United States Patent and Trademark Office*